US006218511B1

(12) United States Patent
Goldmakher et al.

(10) Patent No.: US 6,218,511 B1
(45) Date of Patent: Apr. 17, 2001

(54) ANTI-APOPTOTIC GENES OF HUMAN CYTOMEGALOVIRUS (HCMV) AND THEIR USE

(75) Inventors: Viktor S. Goldmakher, Newton; Anna Skaletskaya, Milton; Laura Bartle, Arlington, all of MA (US)

(73) Assignee: Apoptosis Technology, Inc., Cambridge, MA (US)

( * ) Notice: Subject to any disclaimer, the term of this patent is extended or adjusted under 35 U.S.C. 154(b) by 0 days.

(21) Appl. No.: 09/080,265

(22) Filed: May 18, 1998

(51) Int. Cl.[7] .................................................. A61K 39/245
(52) U.S. Cl. ............................................. 530/350; 514/12
(58) Field of Search ................................ 530/350; 514/12

(56) References Cited

U.S. PATENT DOCUMENTS 5,656,725    8/1997    Chittenden et al. .

FOREIGN PATENT DOCUMENTS

| WO 96/30404 | 10/1996 | (WO) . |
| WO 97/12632 | 4/1997  | (WO) . |
| WO 97 15326 | 5/1997  | (WO) . |

OTHER PUBLICATIONS

Colberg–Poley, A.M. et al. Human Cytomegalovirus US3 and UL36–38 Immediate–Early Proteins Regulate Gene Expression. J. Virol. 66(1):95–105, 1992.*

Colbert–Poley, A.M. Functional Roles of Immediate Early Proteins Encoded by the Human Cytomegalovirus UL36–38, UL115–119, TRS1/IRS1 and US3 Loci. Intervirology 39:350360, 1996.*

Tony Kouzarides et al. "An Immediate Early Gene of Human Cytomegalovirus Encodes a Potential Membrane Glycoprotein" *Virology* 165: 151–164 (1988).

Hebah O. Al–Barazi and Anamaris M. Colberg–Poly "The Human Cytomegalovirus UL37 Immediate–Early Regulatory Protein Is an Integral Membrane N–Glycoprotein Which Traffics through the Endoplasmic Reticulum and Golgi Apparatus" *J. Virol.* 70: 7198–7208 (1996).

Daniel J. Tenney and Anamaris M. Colberg–Poley "Expression of the Human Cytomegalovirus UL36–38 Immediate Early Region during Permissive Infection" *Virology* 182: 199–210 (1991).

\* cited by examiner

*Primary Examiner*—Donna C. Wortman
(74) *Attorney, Agent, or Firm*—Sughrue, Mion, Zinn, Macpeak & Seas, PLLC

(57) ABSTRACT

Disclosed are compositions and methods of screening for targets for antiviral chemotherapy having anti-apoptotic activity, and compositions and methods of screening for antiviral compounds that interfere with the anti-apoptotic activity of such targets. The targets comprise viral polypeptides having anti-apoptotic activity, and polynucleotides encoding such polypeptides. An example of such targets is a group of viral polypeptides of human cytomegalovirus (HCMV) having anti-apoptotic activity, such as pUL36, pUL37$_S$, and pUL37$_L$, and the polynucleotides encoding such polypeptides. The antiviral compounds comprise polypeptide, polynucleotide, DNA, RNA, amino acid, nucleic acid, and chemical compositions, including the chemically modified forms of such compositions, that interfere with the anti-apoptotic function of the target polypeptides and polynucleotides, leading to the induction of apoptosis and, consequently, the prevention or inhibition of replication.

1 Claim, 10 Drawing Sheets

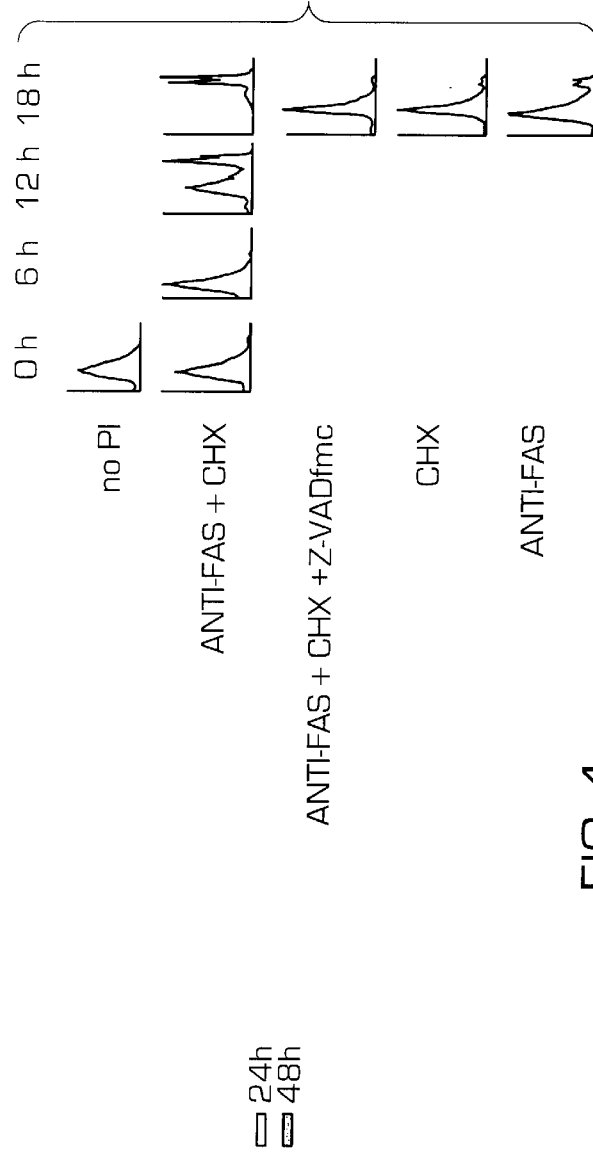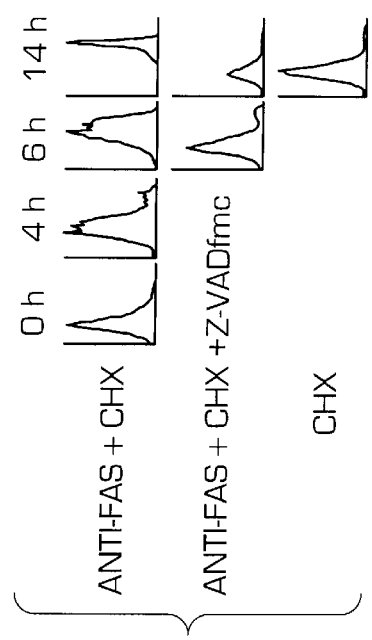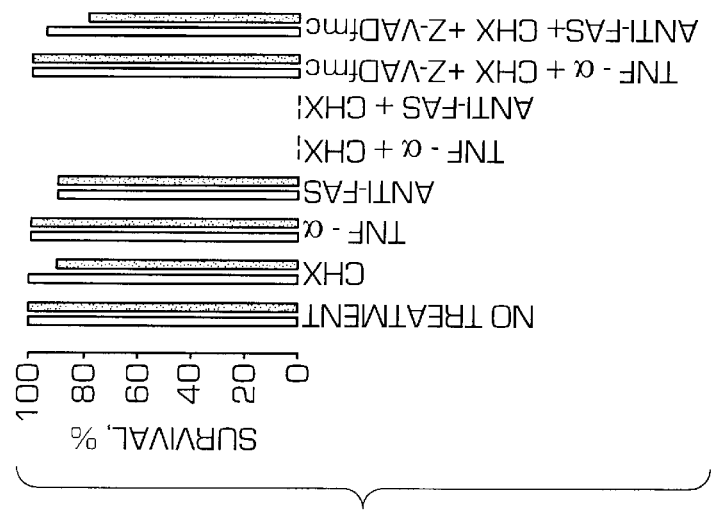

NON-INFECTED CELLS

CMV-INFECTED CELLS

US 6,218,511 B1

ANTI-APOPTOTIC GENES OF HUMAN CYTOMEGALOVIRUS (HCMV) AND THEIR USE

FIELD OF THE INVENTION

The present invention relates to novel compositions and methods of screening for targets for antiviral chemotherapy having anti-apoptotic activity, and compositions and methods of screening for antiviral compounds that interfere with the anti-apoptotic activity of such targets. The targets comprise viral polypeptides having anti-apoptotic activity, and polynucleotides encoding such polypeptides. Examples of such targets are viral polypeptides of human cytomegalovirus (HCMV) having anti-apoptotic activity, such as pUL36, pUL37$_S$, and pUL37$_L$, and the polynucleotides encoding such polypeptides. The antiviral compounds comprise polypeptide, polynucleotide, DNA, RNA, amino acid, nucleic acid, and chemical compositions, including modified forms of such compositions, that interfere with the anti-apoptotic function of the target polypeptides and polynucleotides, leading to the induction of apoptosis and, consequently, the prevention or inhibition of replication.

BACKGROUND OF THE INVENTION

Human cytomegalovirus (HCMV) is widespread in human populations (Britt and Alford, 1996). Congenitally infected newborns and immunocompromised individuals, such as those undergoing organ transplants and those with malignancies receiving immunosuppressive chemotherapy, and particularly patients with AIDS, are at greatest risk of HCMV-induced diseases. These diseases range from developmental abnormalities, mental retardation, deafness, mononucleosis, chorioretinitis to fatal diseases like interstitial pneumonitis and disseminated HCMV infections (Huang and Kowalik, 1993; Britt and Alford, 1996).

Antiviral treatments seek to prevent or arrest viral replication. Today there are only very limited treatment options available for cytomegalovirus infections, and treatment is often associated with high toxicity and the generation of drug resistance (Hirsch, 1994; White and Fenner, 1994; Lalezari et al., 1997). Several potential drug development targets for herpesviruses have been identified (White and Fenner, 1994, page 267, Table 16.1). Currently available agents, Gancyclovir, Foscarnet (PFA, phosphonoformic acid) and Cidofovir all act as inhibitors of viral DNA polymerase.

Animals and humans have developed an intricate system of defenses against viral infections. One important defense mechanism activates the cellular suicide program, or apoptosis, in the virally-infected host cell, thereby preventing the replication of the virus. Conversely, viruses have evolved to overcome the defenses of the host. Of particular interest, in the context of this application, is that many viruses have evolved to carry genes that can prevent or retard the onset of apoptosis in the virally-infected cells. This inhibition of apoptosis by viral gene products is achieved by a variety of mechanisms, examples of which include: 1) blocking and/or destruction of p53; 2) direct interaction with cellular polypeptides of apoptotic pathways, such as death-effector-domain-containing polypeptides [death-effector-domain motifs are defined in Hu et al., J. Biol. Chem. 272, 9621–9624 (1997)], Bcl-2 family members and caspases; or 3) by induction of cellular anti-apoptotic polypeptides (Pilder et al., 1984; Gooding et al., 1988; Clem et al., 1991; Hershberger et al., 1992; Brooks et al., 1995; Sedger and McFadden, 1996; Leopardi and Roizman, 1996; Leopardi et al., 1997; Razvi and Welsh, 1995; Teodoro and Branton, 1997; Vaux et al., 1994; Shen and Shenk, 1995; Duke et al., 1996; Vaux and Strasser, 1996; Thompson, 1995). Some of these anti-apoptotic genes were found to be essential for the ability of the respective viruses to replicate and propagate. For example, mutants of human adenovirus that lack the expression of the E1B 19 kDa adenoviral analog of Bcl-2 induce massive apoptosis of infected cells (Teodoro and Branton, 1997) which, consequently, leads to reduced viral titers.

HCMV is a herpesvirus (Roizman, 1991). A number of herpesviruses were shown to induce an apoptotic host cell response, and to suppress this virus-induced apoptosis in the infected cells (Leopardi and Roizman, 1996; Leopardi et al., 1997; Bertin et al., 1997; Sieg et al., 1996). The genomes of several herpesviruses code for a variety of anti-apoptotic polypeptides such as: 1) Bcl-2 homologs, e.g., BHRF-1 of Epstein-Barr virus (Henderson et al., 1993), vbcl-2 of Kaposi's sarcoma-associated herpesvirus (Sarid et al., 1997), and ORF16 of herpesvirus Saimiri (Nava et al., 1997); 2) a polypeptide which induces several cellular anti-apoptotic genes, e.g., LMP-1 of Epstein-Barr virus (Henderson et al., 1991; Wang et al., 1996; Fries et al., 1996); 3) a polypeptide interacting with FLICE (also called caspase-8), e.g., Equine herpesvirus type 2 polypeptide E8 (Bertin et al., 1997; Hu et al., 1997); and 4) two polypeptides with anti-apoptotic properties with a yet poorly characterized mechanism, ICP4 and U$_S$3 of HSV-1 (Leopardi and Roizman, 1996; Leopardi et al., 1997). However, little is known about the ability of HCMV to regulate apoptosis in HCMV-infected cells.

The HCMV genome (AD 169 strain) has been completely sequenced (Chee et al. 1990; Mocarski, 1996). From the sequence, 208 ORFs (open reading frames) of greater than 300 base pair lengths were predicted and given names. However, for many of these ORFs the predicted corresponding polypeptides have not been directly identified. Whether most of these genes are expressed and have any functional importance for HCMV replication remains unknown. In fact, a number of these ORFs were found to be dispensable for the replication and/or propagation of HCMV in cultured cells (Mocarski, 1996).

Although Zhu et al. (1995) proposed that two polypeptides encoded in the HCMV genome, IE1 and IE2, have an anti-apoptotic activity in HeLa cells, these data were not independently confirmed by other researchers. Moreover, the present inventors demonstrated that IE1 and IE2 did not display any anti-apoptotic activity (see below). No other HCMV anti-apoptotic genes have been identified yet, and no homology to any of the known anti-apoptotic polypeptides has been found in the HCMV genome.

Furthermore, little was known about the UL36 and UL37 genes of HCMV. On the basis of DNA sequence analysis and RNA transcription studies, it was predicted that UL36 has two exons which encode a polypeptide product pUL36, and that UL37 encodes two polypeptide products; pUL37$_S$ encoded by the first exon, and pUL37$_L$ encoded by all three exons (Chee et al., 1990; Tenney and Colberg-Poley, 1991a, b). The expression of pUL37$_L$ in HCMV-infected cells has been detected. However, up until now, it has not been clear whether the hypothetical polypeptide pUL37$_S$ was expressed in HCMV-infected cells.

SUMMARY OF THE INVENTION

The present invention relates to the discovery of methods for detecting the anti-apoptotic function of viral polypeptides and their interactions with cellular polypeptides. The present invention further relates to the discovery of several viral polypeptides having anti-apoptotic activity and also the mechanism by which such viral polypeptides function to inhibit apoptosis. In particular, interference with the anti-apoptotic function of viral polypeptides, and the polynucleotides encoding such polypeptides, can lead to the restoration or induction of apoptosis in virally-infected cells and, consequently, prevent or inhibit viral replication. Thus, these findings provide an approach for the rational design of antiviral drugs that interfere with the anti-apoptotic function of viral polypeptides and polynucleotides, thereby leading to the regulation of apoptosis, including the restoration or induction of apoptosis.

Accordingly, the object of the present invention is to provide compositions and methods of screening for targets for antiviral chemotherapy, having anti-apoptotic activity, and compositions and methods of screening for antiviral compounds that interfere with the anti-apoptotic function of such viral targets.

An embodiment of the present invention provides methods for identifying viral polypeptides having anti-apoptotic activity and polynucleotides encoding such polypeptides.

In particular, an embodiment of the present invention provides methods of screening for human cytomegalovirus (HCMV) polypeptides, having anti-apoptotic activity, and polynucleotides encoding such viral polypeptides. Such HCMV polypeptides include, e.g., any polypeptides encoded by UL36, wherein the polynucleotide sequence of UL36 is defined by nucleotides 49,776–48,246 of the HCMV AD169 genome.

More particularly, an embodiment of the present invention provides methods for identifying HCMV polypeptides pUL36, pUL37$_S$ and pUL37$_L$, having anti-apoptotic activity.

Even more particularly, an embodiment of the present invention provides methods for detecting HCMV polypeptides pUL36, pUL37$_S$ and pUL37$_L$, using polyclonal and monoclonal antibodies that specifically bind to at least one of pUL36 (including any unspliced and alternatively spliced variants of the polypeptide encoded by UL36), pUL37$_S$, and pUL37$_L$.

Another embodiment of the present invention provides methods for detecting the anti-apoptotic activity of viral polypeptides. In particular, an embodiment of the present invention provides methods of detecting the anti-apoptotic activity of HCMV polypeptides.

Even more particularly, an embodiment of the present invention provides methods of detecting the anti-apoptotic activity of HCMV polypeptides pUL36, pUL37$_S$ and pUL37$_L$.

Another embodiment of the present invention provides methods of identifying physiological molecules that specifically interact with at least one of HCMV polypeptides pUL36, pUL37$_S$, and pUL37$_L$. Such physiological molecules comprise polypeptide, polynucleotide, DNA, RNA, amino acid, and nucleic acid molecules.

In particular, an embodiment of the present invention provides methods of screening for physiological molecules that specifically bind to at least one of pUL36, pUL37$_S$, and pUL37$_L$, in an in vitro binding assay.

More particularly, an embodiment of the present invention provides methods of screening for physiological molecules that specifically bind to at least one of pUL36 (including any unspliced and alternatively spliced variants of the polypeptide encoded by UL36), pUL37$_S$, and pUL37$_L$, in a double transformation assay.

Another embodiment of the present invention provides methods of screening for antiviral compounds that interfere with the specific interaction of a physiological molecule with at least one of pUL36, pUL37$_S$, and pUL37$_L$. Such antiviral compounds comprise polypeptide, polynucleotide, DNA, RNA, amino acid, nucleic acid, and chemical compositions, including modified forms of such compositions.

In particular, an embodiment of the present invention provides methods of screening for antiviral compounds that diminish the specific binding of a physiological molecule to at least one of pUL36, pUL37$_S$, and pUL37$_L$, in an in vitro binding assay.

More particularly, an embodiment of the present invention provides methods of screening for antiviral compounds that diminish the specific binding of a physiological molecule to at least one of pUL36, pUL37$_S$ and pUL37$_L$, in a double transformation assay.

Another embodiment of the present invention provides methods of screening for antiviral compounds that interfere with the anti-apoptotic activity of viral polypeptides and polynucleotides encoding such polypeptides, in cells. Such antiviral compounds comprise polypeptide, polynucleotide, amino acid, nucleic acid, DNA, RNA, and chemical compositions, including modified forms of such compositions.

In particular, an embodiment of the present invention provides methods of screening for antiviral compounds that diminish the anti-apoptotic activity of HCMV polypeptides, in cells.

More particularly, an embodiment of the present invention provides methods of screening for antiviral compounds that diminish the anti-apoptotic activity of HCMV polypeptides pUL36, pUL37$_S$ and pUL37$_L$, in cells.

Another embodiment of the present invention provides methods of screening for antiviral compounds that regulate apoptosis in cells transformed with a polynucleotide encoding at least one polypeptide having anti-apoptotic activity.

In particular, an embodiment of the present invention provides methods of screening for antiviral compounds that regulate apoptosis in cells transformed with a polynucleotide encoding at least one HCMV polypeptide having anti-apoptotic activity.

More particularly, an embodiment of the present invention provides methods of screening for antiviral compounds that regulate apoptosis in cells transformed with a polynucleotide encoding at least one of HCMV polypeptides pUL36, pUL37$_S$ and pUL37$_L$.

Another embodiment of the present invention provides methods of screening for antiviral compounds that interfere with the anti-apoptotic activity of viral polypeptides, and the polynucleotides encoding such polypeptides, in cells and, thereby, induce apoptosis. Such antiviral compounds comprise polypeptide, polynucleotide, amino acid, nucleic acid, DNA, RNA, and chemical compositions, including modified forms of such compositions.

In particular, an embodiment of the present invention provides methods of screening for antiviral compounds that induce apoptosis in virally infected cells.

More particularly, an embodiment of the present invention provides methods of screening for antiviral compounds that induce apoptosis in cells transformed with a polynucleotide encoding at least one polypeptide having anti-apoptotic activity.

More particularly, an embodiment of the present invention provides methods of screening for antiviral compounds that induce apoptosis in cells transformed with a polynucleotide encoding at least one HCMV polypeptide having anti-apoptotic activity.

Even more particularly, an embodiment of the present invention provides methods of screening for antiviral compounds that induce apoptosis in cells transformed with a polynucleotide encoding at least one of HCMV polypeptides pUL36, $pUL37_S$ and $pUL37_L$.

Another embodiment of the present invention provides targets for anti-viral chemotherapy having anti-apoptotic activity.

In particular, an embodiment of the present invention provides as a target for anti-viral chemotherapy isolated or synthetic polypeptides having anti-apoptotic activity. Such isolated or synthetic polypeptides include pUL36 and $pUL37_S$.

Another embodiment of the present invention provides antiviral compounds that specifically bind to at least one of HCMV polypeptides pUL36, $pUL37_S$ and $pUL37_L$.

In particular, an embodiment of the present invention provides polyclonal and monoclonal antibodies that bind to at least one of HCMV polypeptides pUL36, $pUL37_S$ and $pUL37_L$.

BRIEF DESCRIPTION OF THE DRAWINGS

The foregoing and other objects of the present invention, the various features thereof, as well as the invention itself may be more fully understood from the following description, when read together with the accompanying drawings in which:

FIG. 1A is a histogram and FIGS. 1B and 1C are measurements of cell fluorescence showing the effects of TNF-α and anti-Fas in the presence of cycloheximide (CHX) on the survival of MRC-5 normal human fibroblasts as measured by direct observation and quantitation of cells under a phase microscope (1A), by dye exclusion (propidium iodide/PI) assay on a flow cytometer (1B), and by measuring Annexin V binding to cells (1C).

DETAILED DESCRIPTION OF THE INVENTION

Figure 2:
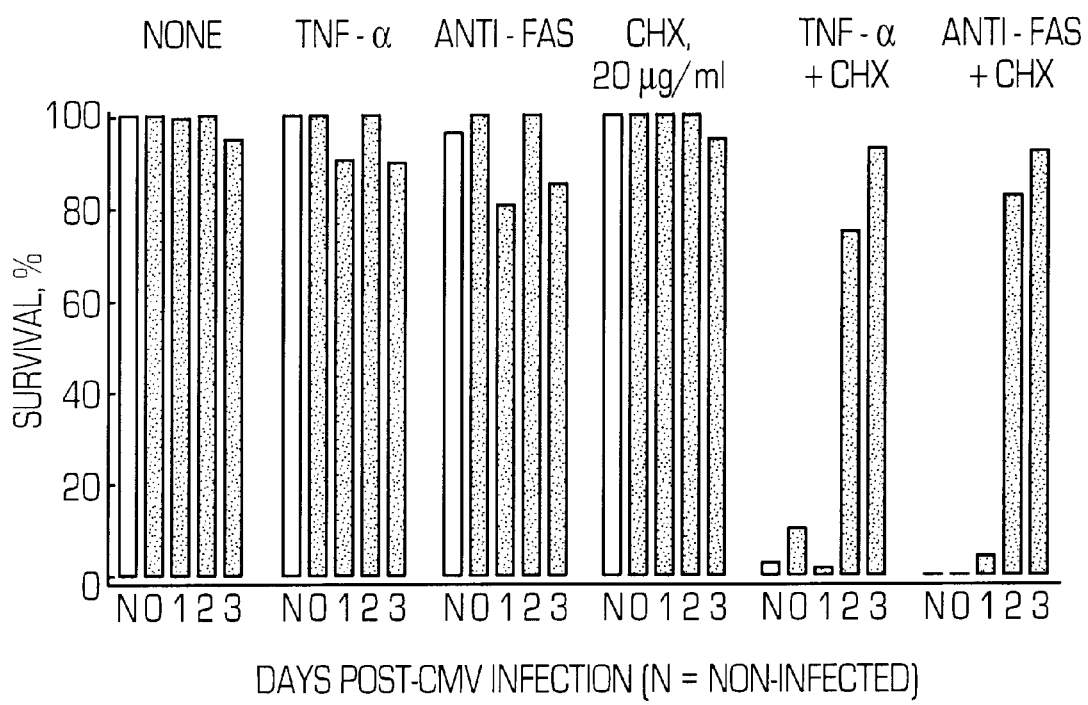
FIG. 2 is a histogram that shows the effects of TNF-α and anti-Fas in the presence of cycloheximide (CHX) on the survival of HCMV-infected MRC-5 normal human fibroblasts.

Targets for Antiviral Chemotherapy Having Anti-apoptotic Activity and Methods of Screening for Such Targets The present inventors have demonstrated that viral infection can result in the inhibition of apoptosis in infected cells. Further, the present inventors have identified viral polypeptides that function to inhibit apoptosis in cells. Such viral polypeptides having anti-apoptotic activity, and the polynucleotides encoding them, are specific targets for the treatment of virally-induced diseases.

For example, antiviral compounds that interfere with the anti-apoptotic function of the target polypeptides, and the polynucleotides encoding such polypeptides, can induce apoptosis in the host cells and, consequently, prevent or inhibit viral replication. The targets for antiviral chemotherapy comprise viral polypeptide, polynucleotide, DNA, RNA, amino acid, and nucleic acid compositions having anti-apoptotic function.

The discoveries of the present inventors provide an approach for the rational design of antiviral drugs. As an example of antiviral targets and methods of screening for such viral targets, the present inventors have screened for and identified human cytomegalovirus (HCMV) polynucleotides encoding polypeptides that function to inhibit apoptosis in host cells. Interfering with the anti-apoptotic function of the identified HCMV polypeptides, and the polynucleotides encoding such polypeptides, can lead to the induction or restoration of apoptosis in the host cells and, consequently, inhibit viral replication. Thus, such anti-apoptotic HCMV polypeptides, and the polynucleotides encoding them, are specific targets for the treatment of virally-induced diseases.

Specifically, the present inventors have demonstrated that HCMV-induced apoptosis is prevented by the expression of HCMV viral genes UL36 and UL37. These findings indicate that polypeptides encoded by UL36 and at least one of the polypeptides encoded by UL37 are essential for preventing virally-induced apoptosis in the infected cells.

More specifically, the present inventors have identified three HCMV polypeptides having anti-apoptotic activity. The three polypeptides are designated pUL36, $pUL37_S$ (S for short, encoded by UL37 exon 1), and $pUL37_L$ (L for long, encoded by UL37 exons 1, 2, and 3). These three HCMV polypeptides, and the polynucleotides encoding them, are specific targets for antiviral chemotherapy. Compounds that specifically interfere with the anti-apoptotic function of pUL36, $pUL37_S$, and $pUL37_L$ can induce apoptosis and, thereby, inhibit viral regulation.

Accordingly, the present invention provides compositions and methods of screening for targets of antiviral chemotherapy, having anti-apoptotic activity. Such targets comprise viral polypeptide, polynucleotide, DNA, RNA, amino acid, and nucleic acid compositions.

Antiviral Compounds and Methods of Screening for Such Compounds

The present inventors have demonstrated that interfering with the anti-apoptotic function of viral polypeptides, and the polynucleotides encoding them, leads to the regulation of apoptosis in the host cells, including the induction of apoptosis, and thereby viral replication is prevented or inhibited. Thus, compounds that interfere with the anti-apoptotic function of the viral polypeptides, and the polynucleotides encoding such polypeptides, are useful for treatment of virally-induced diseases. Such antiviral compounds comprise polypeptide, polynucleotide, DNA, RNA, amino acid, nucleic acid, and chemical compounds, including modified forms of such compounds.

For example, antiviral compounds, such as polyclonal or monoclonal antibodies, can bind directly to the viral polypeptide having anti-apoptotic activity and, thereby, diminish the anti-apoptotic activity of the polypeptide and/or prevent it from specifically interacting with cellular polypeptides or other physiological molecules involved in the apoptosis signalling pathway. Thus, HeLa cells made resistant to apoptosis by stably expressing tagged and non-tagged pUL36 or $pUL37_S$ can be microinjected with a polyclonal or a monoclonal antibody against pUL36 or $pUL37_S$, respectively. This treatment could render the cells susceptible again to apoptosis induced by anti-Fas+CHX. Similarly, microinjections of MRC5 cells infected with HCMV with a polyclonal or a monoclonal antibody against pUL36, $pUL37_S$, or both, could render these cells susceptible again to apoptosis induced by anti-Fas+CHX.

Such physiological molecules comprise polypeptide, polynucleotide, DNA, RNA, amino acid, and nucleic acid molecules. Also, peptide analogs of the viral anti-apoptotic polypeptides can compete for binding with such physiological molecules and, thereby, diminish the anti-apoptotic activity of the viral polypeptide and/or prevent it from specifically interacting with such molecules. As a further example, the antiviral compounds of the present invention can bind directly to the polynucleotide encoding a viral polypeptide having anti-apoptotic activity and, thereby, inhibit the expression of the encoded polypeptide.

Moreover, the present inventors have identified a mechanism by which viral polypeptides function to inhibit apoptosis, and have identified cellular polypeptides that specifically interact with the viral polypeptides having anti-apoptotic activity. Interfering with the mechanism by which a viral polypeptide functions to inhibit apoptosis can diminish anti-apoptosis and/or induce apoptosis and, thus, prevent or inhibit viral replication. Thus, compounds that disrupt the specific interaction of cellular polypeptides with the viral polypeptides having anti-apoptotic activity, are useful for the treatment of virally-induced diseases.

Specifically, the present inventors have demonstrated that $pUL37_S$, $pUL37_L$ and pUL36 interrupt a common, and previously described, apoptotic signalling pathway involving TNF-R1 and Fas (Salversen and Dixit, 1997). The three polypeptides can act by binding to one or several known or yet unknown polypeptides involved in the apoptotic signalling pathway and, thus, interrupt the apoptotic process.

Thus, the present invention teaches an approach to the rational design of antiviral drugs. Antiviral compounds that bind to at least one of pUL36, $pUL37_S$, and $pUL37_L$ and prevent such viral polypeptides from interacting with the polypeptides of the apoptotic pathway, can induce apoptosis in HCMV-infected cells and, thereby, prevent viral replication. Such antiviral compounds selectively interact with viral and not cellular polypeptides. Consequently, such compounds are useful in the treatment of virally-induced diseases.

Also specifically, the present inventors have identified a mechanism by which $pUL37_S$ and pUL36 function to inhibit apoptosis. The viral polypeptide $pUL37_S$ acts by binding to FADD, FLICE, Caspase 3 (cpp32), Apaf-1, Bcl-$x_L$, Bcl-2, Bak, ICE, Bax, and BNIP3, thus, interrupting the apoptosis-signalling pathway between FADD and FLICE, FLICE and Caspase 3 (cpp32), FLICE and Apaf-1, different or the same Bcl-2-family members, Bcl-2 family members and Apaf-1, and between any of the above polypeptides and any known or not yet discovered polypeptides involved in apoptotic signalling pathways. The viral polypeptide pUL36 acts as an inhibitor of caspases, thus, interrupting the apoptosis signalling pathway.

Thus, the present invention teaches antiviral compounds, and methods of screening for antiviral compounds, that bind to pUL36 or $pUL37_S$ and prevent its interaction with FADD, FLICE, Caspase 3 (cpp32), Apaf-1, Bcl-$x_L$, Bcl-2, Bak, ICE, Bax, BNIP-3, or any yet undiscovered anti-apoptotic polypeptide interaction of which with pUL36 and $pUL37_S$ can be detected in a binding assay. Also, the present invention teaches antiviral compounds, and methods of screening for antiviral compounds, that bind to pUL36 and prevent its interaction with caspases. Such antiviral compounds interfere with the anti-apoptotic function of the viral polypeptides, leading to the induction of apoptosis in HCMV-infected cells and, consequently, prevent or inhibit viral replication. Further, such antiviral compounds can specifically interact with viral and not cellular polypeptides and, therefore, cannot affect the non-infected cells.

Accordingly, the present invention teaches antiviral methods for detecting the specific interaction of a physiological molecule with at least one of $pUL37_S$, $pUL37_L$ and pUL36. Such physiological molecules comprise polypeptide, polynucleotide, DNA, RNA, amino acid, and nucleic acid molecules. Such methods are useful in the discovery of antiviral compounds that interfere with the specific interaction of a physiological molecule with at least one of the identified HCMV polypeptides having anti-apoptotic activity and, thereby, induce apoptosis and prevent or inhibit viral replication.

Further, the present invention teaches antiviral compounds, and methods of screening for antiviral compounds, that specifically bind to at least one of $pUL37_S$, $pUL37_L$ and pUL36 and interfere with the anti-apoptotic function of the viral polypeptides, thereby leading to the induction of apoptosis in the host cell and, thus, preventing or inhibiting viral replication. The antiviral compounds can interfere with the anti-apoptotic function of the viral polypeptides, and the polynucleotides encoding them, for example, by: 1) diminishing the specific binding of a physiological molecule to an identified viral polypeptide having anti-apoptotic activity; 2) diminishing the anti-apoptotic activity of a viral polypeptide, or polynucleotide encoding the polypeptide, in the host cells; and 3) regulating apoptosis, e.g., inducing apoptosis, in the host cells. Such antiviral compounds comprise polypeptide, polynucleotide, DNA, RNA, amino acid, nucleic acid, and chemical compounds, including modified forms of such compounds.

Further, the present invention teaches that an effective antiviral compound is one that can selectively interfere with the anti-apoptotic function of viral polypeptides and, thus, restore or induce apoptosis in the host cells.

Accordingly, the present invention provides compositions and methods of screening for antiviral compounds that interfere with the anti-apoptotic function of viral polypeptides and the polynucleotides encoding such polypeptides. Such antiviral compounds comprise polypeptides, polynucleotides, DNA, RNA, amino acid, nucleic acid, and chemical compositions, including modified forms of such compositions.

DESCRIPTION OF THE EMBODIMENTS

Generally, the nomenclature used hereafter and the laboratory procedures in cell culture, molecular genetics, and nucleic acid chemistry and hybridization described below are those well known and commonly employed in the art. Standard techniques are used for in vitro and in vivo binding assays, recombinant nucleic acid methods, polypeptide and polynucleotide synthesis, microbial culture and transformation and mammalian cell culture, transfections and retroviral vector transductions.

Generally, enzymatic reactions and purification steps are performed according to the manufacturer's specifications. The techniques and procedures are generally performed according to conventional methods in the art and various general references (see, generally, Sambrook et al. Molecular Cloning: A Laboratory Manual, 2 d ed. (1989) Cold Spring Harbor Laboratory Press, Cold Spring Harbor, N.Y., which is incorporated herein by reference) which are provided throughout this document. The procedures therein are believed to be well known in the art and are provided for the convenience of the reader. All the information contained therein is incorporated herein by reference.

The term "polypeptide" is used herein as a generic term to refer to an isolated or synthetic protein and fragments, oligos, amino acids, and analogs thereof. A polypeptide may also refer to the full-length protein encoded by a gene and fragments, oligos, amino acids, and analogs thereof. Hence, protein and fragments, oligos, and analogs thereof are species of the polypeptide genus. Preferred polypeptides include pUL36 (including any unspliced and alternatively spliced variants of the polypeptide encoded by UL36), $pUL37_S$, and $pUL37_L$ having anti-apoptotic activity.

The term "amino acid" is used herein to denote at minimum a single amino acid. A preferred amino acid is one that can bind to a polypeptide having anti-apoptotic activity and interfere with, e.g., diminish, such activity.

The term "polynucleotide" is used herein as a generic term to refer to an isolated or synthetic DNA or RNA, and fragments, oligos, nucleic acids, and analogs thereof. Polynucleotide may also refer to a gene or the full-length RNA transcribed from a gene, and fragments, oligos, nucleic acids, and analogs thereof. Hence, DNA and RNA, and fragments, oligos, nucleic acids, and analogs thereof are species of the polynucleotide genus. Preferred polynucleotides include UL36 and UL37.

The term "nucleic acid" is used herein to denote both deoxynucleotide triphosphates (dNTPs) and ribonucleotide triphosphates (rNTPs). A preferred nucleic acid is a dNTP or rNTP that can bind to a polypeptide having anti-apoptotic activity and interfere with, e.g., diminish, such activity.

The term "physiological molecule" is used herein as a generic term to refer to a naturally occurring molecule found in a cell such as, a polypeptide, polynucleotide, DNA, RNA, amino acid, and nucleic acid. Preferred physiological molecules are FADD, FLICE, Caspase 3 (cpp32), Apaf-1, Bcl-$x_L$, Bak, ICE, Bax, and BNIP-3.

The term "accessory" is used herein to denote those physiological molecules that specifically bind to viral polypeptides having anti-apoptotic activity. Such accessory molecules include polypeptide, polynucleotide, DNA, RNA, amino acid, and nucleic acid molecules. Preferred accessory polypeptides are FADD, FLICE, Caspase 3 (cpp32), Apaf-1, Bcl-$x_L$, Bcl-2, Bak, ICE, Bax, and BNIP-3.

The term "compound" is used herein to denote a chemical or biological macromolecule including but not limited to, polypeptide, polynucleotide, DNA, RNA, amino acid, nucleic acid compositions, and chemically and genetically modified forms of such compositions.

Detecting the Expression of Viral Polypeptides

Expression of viral polypeptides, such as HCMV polypeptides, in cells can be detected by a variety of standard protocols for detecting polypeptides known to those skilled in the art. For example, viral polypeptides can be detected by Western Blot analysis with a polyclonal or monoclonal antibody that recognizes and binds to the viral polypeptides. The antibody can be tagged at the amino- or carboxyl-terminus with a molecule that facilitates detection of the viral polypeptide bound to the antibody. Further, viral polypeptides can be detected by immunofluorescence using a polyclonal or monoclonal antibody that recognizes and binds to the viral polypeptides. Fluorescence of the bound antibody can be generated by tagging the primary antibody with a fluorescent molecule or binding a secondary antibody containing a fluorescent molecule to the primary antibody. Such methods are described in Current Protocols in Molecular Biology, John Wiley & Sons, 1998; Current Protocols in Immunology, John Wiley & Sons, 1998; the Invitrogen catalogue, 1998; and the Kodak Scientific Imaging Systems Catolog, 1996/1997; each of which is incorporated herein by reference.

A preferred embodiment is the expression of $pUL37_S$ in HCMV-infected mammalian cells, for example MRC-5 cells, detected by Western Blot analysis with rabbit polyclonal antibodies that recognize KLH-conjugated polypeptides corresponding to the C-terminal amino acids of $pUL37_S$, wherein such antibodies also recognize $pUL37_L$.

Another preferred embodiment is the expression of pUL36 in HCMV-infected mammalian cells, for example MRC-5 cells, detected by Western Blot analysis with rabbit polyclonal antibodies that recognize KLH-conjugated polypeptides corresponding to pUL36.

Methods of Detecting Anti-apoptotic Activity

Apoptosis can be induced in cells by treating the cells with an agent that leads to cell death. Suitable agents include, but are not limited to, those agents that bind to a Fas Receptor (Fas), a tumor necrosis factor receptor (TNFR), or activate the caspase signal transduction pathway for apoptosis. For example, tumor necrosis factor receptor-1 (TNF-R1)-mediated apoptosis can be induced by exposure of cells, such as MRC-5 cells, to TNF-α in the presence of cycloheximide (CHX). Alternatively, Fas-mediated apoptosis can be induced by exposure of cells to anti-Fas antibody in the presence of CHX. The degree of cell death or apoptosis can then be measured by a variety of methods such as those described in Sellers, J. R., Cook, S., and Goldmacher, V. S. J. Immunol. Meth. 172, 255–264 (1994) and references cited therein; Telford, W. G., King, L. E., and Fraker, P. J., J. Immunol. Meth. 172, 1–16 (1994) and references cited therein; Apoptosis Techniques and Protocols, Poirier, J. (ed.), Humana Press, Totowa, N.J., 1997; each of which is incorporated herein by reference. Also such methods include those described below, such as the direct visual scoring of surviving cells under a phase microscope.

Further, the time course of apoptosis can be analyzed by measuring the level of expression of phosphatidylserine on the cell surface, as detected, for example, with FITC-labeled Annexin V, and/or by a dye-exclusion test using propidium iodide. These two tests can be performed using a commercially available kit, for example, the ApoAlert Annexin V Apoptosis kit (Clontech), in accordance with the manufacturer's recommendations, and using a flow cytometer (FACScan, Becton-Dickinson) or fluorescent microscope.

Furthermore, the cells can be transfected with an indicator plasmid carrying a reporter gene encoding an indicator molecule, and the degree of cell death or apoptosis measured by detection of the expressed indicator molecule. For example, the degree of apoptosis in cells transfected with an indicator plasmid expressing the indicator *E. coli* β-galactosidase can be determined by a β-galactosidase ELISA (Boehringer Mannheim), in accordance with the manufacturer's recommendations. Also, the degree of apoptotic activity can be determined by visually scoring, under a microscope, blue cells expressing β-galacotosidase, after staining them with X-gal. As another example, the degree of apoptosis in cells transfected with an indicator plasmid expressing Green Fluorescent Protein can be determined by measuring the fraction of fluorescent cells in the total cell population, using a flow cytometer (FACScan, Becton-Dickinson) or fluorescent microscope.

Further, DNA degradation, indicative of apoptosis, can be examined by exposing the cells to anti-Fas in the presence of CHX. Thereafter, the DNA in the cells is extracted and purified using standard protocols. Any methods detecting cell death or apoptosis can be used such as those described in Sellers, J. R., Cook, S., and Goldmacher, V. S. J. Immunol. Meth. 172, 255–264 (1994) and references cited therein; Telford, W. G., King, L. E., and Fraker, P. J., J. Immunol. Meth. 172, 1–16 (1994) and references cited therein; Apoptosis Techniques and Protocols, Poirier, J. (ed.), Humana Press, Totowa, N.J., 1997; each of which is incorporated herein by reference.

Accordingly, the anti-apoptotic activity of viral polypeptides, i.e., the inhibition or diminution of apoptotic activity, can be detected by measuring the relative levels of apoptotic activity exhibited in one portion of a cell culture transfected with viral polynucleotides encoding at least one polypeptide having anti-apoptotic activity, compared to a second portion of the same cell culture that is not transfected, or is transfected with polynucleotide that does not encode a polypeptide having anti-apoptotic activity (control cells).

For example, one portion of a cell culture can be transfected with a fragment of a HCMV polynucleotide encoding a polypeptide having anti-apoptotic activity. Whereas, a second portion of the same cell culture can be transfected with a polynucleotide that does not encode a polypeptide having anti-apoptotic activity (control cells). Anti-apoptotic activity, i.e., the inhibition or diminution of apoptosis, can then be detected by comparing the degree of apoptotic activity detected in the portion of cells transfected with the viral polynucleotide relative to the degree of apoptotic activity detected in the control cells.

A preferred embodiment is a method of detecting the apoptotic activity of HCMV-infected cells or host cells transfected with a fragment of HCMV encoding at least one of pUL36 (including any unspliced and alternatively spliced variants of the polypeptide encoded by UL36), pUL37$_S$, and pUL37$_L$.

Compositions and Methods of Screening for Viral Polypeptides Having Anti-apoptotic Activity Various methods can be employed to induce apoptosis. For example, the host cells can be treated with anti-Fas antibodies or treated with tumor necrosis factor-α (TNF-α). Both methods of treatment activate the apoptotic signaling pathways involved in the elimination of virally-infected cells in the host animals (Mestan et al., 1986; Vilcek and Sen, 1996; Wong et al., 1986; Kagi et al., 1994; Sieg, et al., 1996; Razvi and Welsh, 1995; each of which is incorporated herein by reference).

Transfection of mammalian cells with viral polynucleotides encoding viral polypeptide can prevent anti-Fas- and TNF-α-induced apoptosis. Protection of the host cells from apoptosis indicates that viral gene products, e.g., anti-apoptotic viral polypeptides, prevent apoptosis induced by anti-Fas and TNF-α and, consequently provides a method of screening for viral polynucleotides encoding polypeptides having anti-apoptotic activity.

In a preferred embodiment, transfection of cells with HCMV polynucleotide prevents anti-Fas- and TNF-α-induced apoptosis. Protection of the host cells from apoptosis indicates that HCMV anti-apoptotic polypeptides prevent apoptosis induced by anti-Fas and TNF-α and, consequently, provides a method of screening for HCMV polynucleotides encoding polypeptides having anti-apoptotic activity, such as pUL36 (including any unspliced and spliced variants of the polypeptide encoded by UL36), pUL37$_S$, and pUL37$_L$.

In a preferred embodiment, HeLa cells transfected with a viral polynucleotide, encoding a polypeptide, are exposed to the anti-Fas monoclonal antibody 7C11 or to TNF-α, and cell death is measured by visual scoring of the cells under a phase microscope. Alternatively, the induced cell death or apoptosis of the HeLa cells, can be examined by a dye-exclusion test on a flow cytometer.

Fas-mediated apoptosis is accompanied by the characteristic apoptotic events: 1) surface blebbing, as observed under a phase microscope (not shown); 2) emergence of phosphatidylserine, an early marker of apoptosis in the outer layer of the cell plasma membrane (FIG. 1C); 3) DNA degradation (not shown); and 4) protection by a caspase inhibitor, for example Z-VADfmc (FIGS. 1A–C).

In the course of viral infection, the cells can gradually develop resistance to TNF-R1 and Fas-mediated apoptosis. Although early in viral infection, i.e., on day 0 and day 1 of infection, the cells can still be sensitive to TNF-α- and anti-Fas-induced apoptosis. By day 2 most of the cells in the infected culture can become insensitive to these stimuli, which is evident by microscopic examination of cell death (FIG. 2). A flow-cytometric PI dye-exclusion test and the test for the surface expression of phosphatidylserine by apoptotic cells can confirm that a major fraction of virally-infected cells (72 h post-infection) retain their capacity to exclude the dye, and not express phosphatidylserine following their exposure to anti-Fas+CHX (data not shown). Thus, such findings provide a method of screening for viral polypeptides having anti-apoptotic activity and viral polynucleotides encoding such polypeptides.

A preferred embodiment is a method of screening for HCMV polypeptides having anti-apoptotic activity and HCMV polynucleotides encoding such polypeptides. An example of such HCMV polypeptides is pUL36 (including any unspliced and alternatively spliced variants of the polypeptide encoded by UL36), pUL37$_S$, and pUL37$_L$.

Suitable candidate polypeptides can be identified by using an assay where an increased expression of a marker gene product, such as β-galactosidase or a fluorescent polypeptide, is indicative of anti-apoptotic activity. In such an assay, a first portion of cells from a culture of cells is co-transfected with an expression plasmid encoding a marker polypeptide and an expression plasmid vector containing a DNA insert encoding a candidate polypeptide. In parallel, as a control, a second portion of cells from the same culture is co-transfected with the expression plasmid encoding a marker polypeptide and the "empty" expression plasmid vector which lacks the DNA insert encoding a candidate polypeptide ("empty vector").

The cells are then treated with an agent, such as anti-Fas antibody or TNF-α, under conditions that induce apoptosis. The expression of the marker polypeptide in the induced cells is then measured after a sufficient amount of time for apoptosis to be completed (typically overnight). Any candidate polypeptide encoded by the DNA insert contained in the plasmid expression vector that supports the increased expression of the marker polypeptide compared to that of the empty vector is then selected as a candidate polypeptide and subjected to further testing for anti-apoptotic activity.

Figure 6:
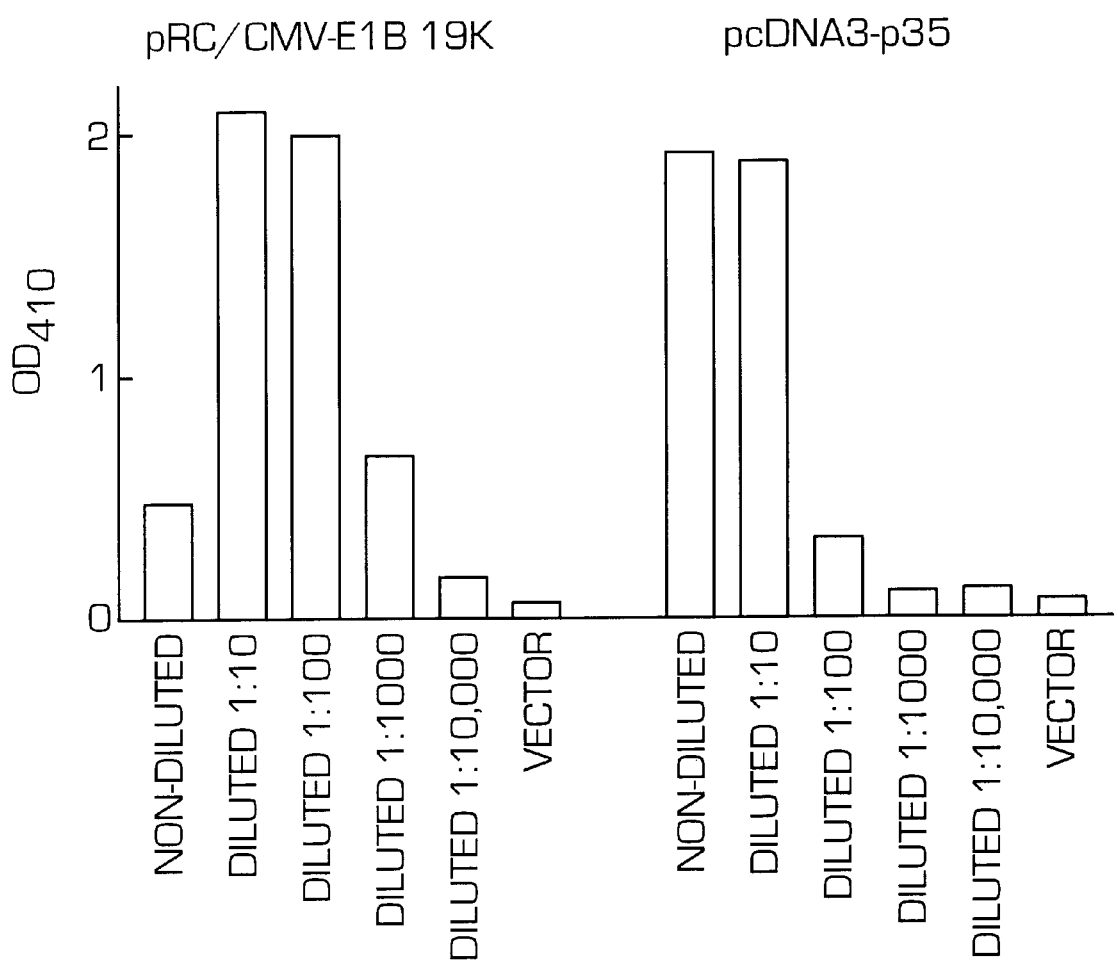
FIG. 6 is a histogram that shows the protection of populations of HeLa cells from anti-Fas/CHX-induced apoptosis by transfection with different amounts of an expression plasmid carrying the EIB 19K gene.
Figure 7:
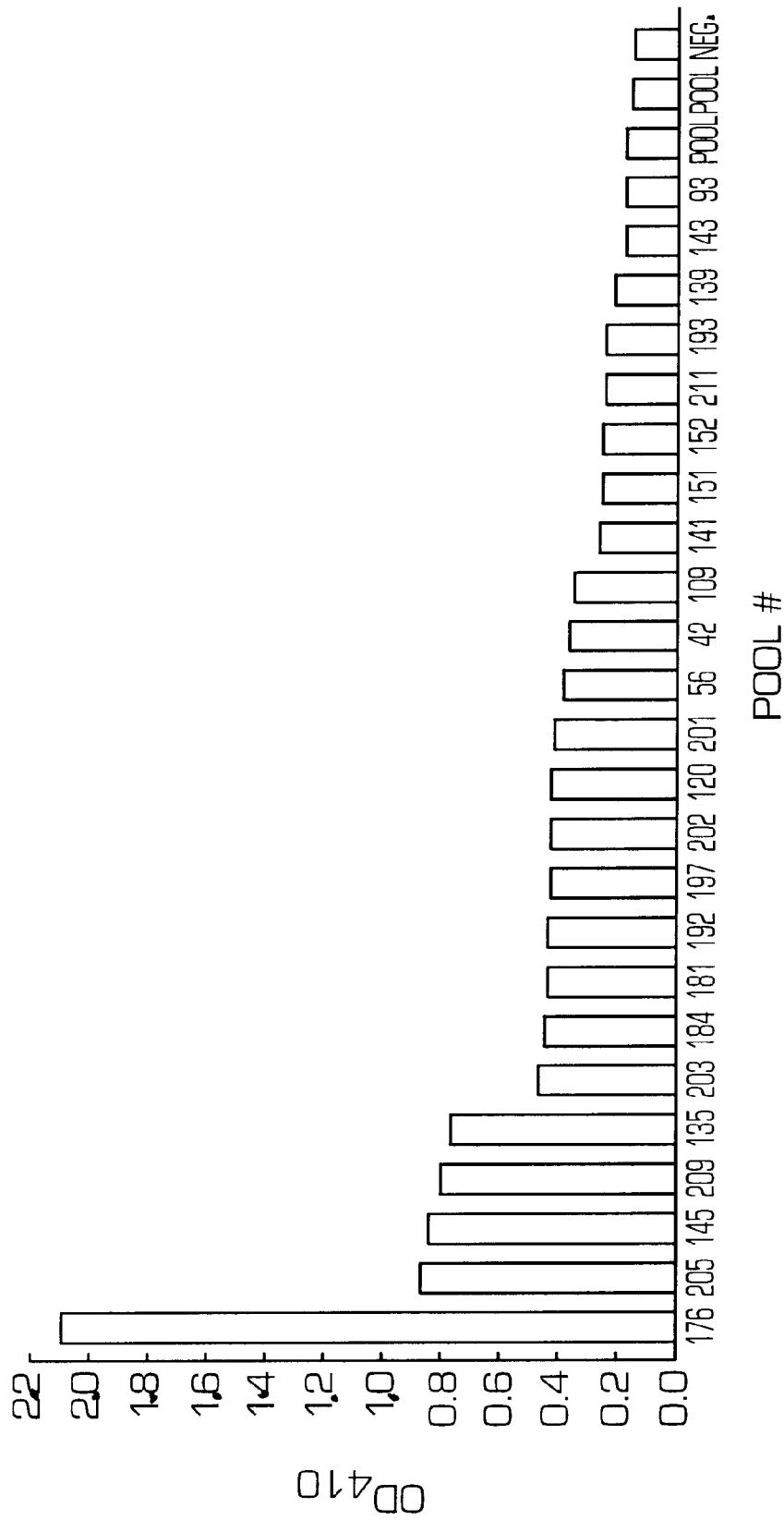
FIG. 7 is a histogram that represents the results of screening genomic CMV library plasmid pools for their anti-apoptotic activity in HeLa cells treated with anti-Fas and cycloheximide (CHX).

Two examples of known anti-apoptotic polypeptides, the adenoviral E1B 19k and the baculoviral p35, that were subjected to such an assay are shown in FIG. 6. The results of the assay indicate that the E1B 19K sample diluted 1:10,000 with the empty vector is a suitable candidate for additional testing and illustrate the utility of such an assay in identifying suitable candidate polypeptides. Similarly, FIG. 7 shows the results of such an assay performed on expression plasmid vectors containing HCMV genomic DNA inserts encoding candidate polypeptides. Any pool of plasmids expressing a level of the marker gene product above background encode candidate polypeptides that are to be tested further for anti-apoptotic activity (see text below for further details).

Compositions and Methods of Screening a DNA Library for Viral Polynucleotides Encoding Polypeptides Having Anti-apoptotic Activity To screen for and identify viral polynucleotides encoding a polypeptide having anti-apoptotic activity, a DNA library transfected into mammalian cells, for example HeLa cells, can be screened. The ability of the HeLa cells to undergo Fas- or TNF-R1-mediated apoptosis is similar to that of MRC-5 fibroblasts. HeLa cells undergo apoptosis when exposed to either an anti-Fas antibody+CHX, or TNF-α+CHX. In a preferred embodiment anti-Fas antibodies, 7C11 is used to induce apoptosis in HeLa cells, in the presence of CHX.

In order to construct a DNA library, viral polynucleotide is partially digested with at least one restriction enzyme and then ligated into a plasmid expression vector. For example, viral DNA can be partially digested with Sau3AI and ligated into the pZeoSV2(+) plasmid expression vector. The average insert size of the library is typically 3.5 kb (the range 1.7–13 kb).

In a preferred embodiment, the DNA library is constructed using HCMV DNA. The sequences of most of the predicted HCMV genes either contain no introns or contain exons that are located in close proximity to each other (Chee et al., 1990, which is incorporated herein by reference). Consequently, HCMV DNA containing a full-length gene sequence may be represented in a single plasmid, in a library containing an average insert size of 3.5 Kb.

The screening of the library is based on the present inventors' finding that even a very low concentration (e.g., as low as 0.1% to 1% of the total DNA transfected) of a transfected expression plasmid carrying an anti-apoptotic gene, such as adenoviral E1B 19K, baculovirus p35 (FIG. 6), human BCL-$X_L$, or human BCL2, mixed with a high concentration of a control vector, that does not encode a polypeptide having anti-apoptotic activity, offered a detectable protection of HeLa cells against anti-Fas-induced apoptosis in the presence of CHX. Thus, in the preferred embodiment, 212 pools of the library plasmids (with an average complexity of 500 colonies/pool) are prepared and the anti-apoptotic activity of these pools of plasmids compared in HeLa cells. The pools giving the strongest β-galactosidase signals, are then divided into lower complexity sub-pools and evaluated in a similar test.

Finally, individual plasmids from the sub-pools with the highest β-galactosidase activity are re-tested, and those possessing anti-apoptotic activity are isolated. Positive isolates exhibit strong anti-apoptotic activity comparable to those plasmids carrying the BCL-$X_L$ and E1B 19K genes introduced into cells by a similar transient transfection protocol. For example, 5 to 15% of cell populations transiently transfected with plasmids carrying the BCL-$X_L$ and E1B 19K genes survive apoptosis induced by anti-Fas+CHX, while nearly all cells (greater than 99.9%) in control cultures transfected with the control vector die, as observed under a microscope.

The DNA inserts of the positive clones can be identified by polynucleotide sequencing. In a preferred embodiment, these inserts represent two regions of the HCMV genome. The first region contains exon 1 of the UL37 gene with a hypothetical ORF between nucleotides 52,706–52,215 of the complementary strand of the AD169 genome (Tenney and Colberg-Poley, 1991a,b) coding for a potential polypeptide which is designated as pUL37$_S$. S stands for "short" since UL37 codes for another polypeptide product, pUL37$_L$ ("long") translated from a spliced mRNA covering UL37 exons 1, 2, and 3. The second region contains an ORF encoded on the complementary strand in exons 1 and 2 of UL36 representing nucleotides 49,776–48,246 of the AD169 genome (Tenney and Colberg-Poley, 1991a,b). The polypeptide pUL36 is encoded within this region. In addition, variants of pUL36, including unspliced and alternatively spliced variants of pUL36, or other polypeptides may be encoded within this region.

The polypeptide pUL37$_L$ has been previously reported to be expressed by human cells infected with HCMV, and it has been proposed that most of the exon 1 sequence has no functional significance for replication of HCMV transactivating activity or intracellular localization (Zhang et al., 1996, which is incorporated herein by reference). Moreover, neither the expression of the hypothetical polypeptide pUL36 in any cells nor its possible function has been reported.

A preferred embodiment is a method of screening for HCMV polynucleotides encoding polypeptides having anti-apoptotic activity.

Cloning of Polynucleotides Encoding a Polypeptide Having Antiapoptotic Activity

Genomic or cDNA clones encoding an anti-apoptotic polypeptide may be isolated from clone libraries (e.g., OriGene Technologies, Inc., Rockville, Md.) using hybridization probes designed on the basis of known nucleotide sequences and using conventional hybridization screening methods (e.g., Benton W. D. and Davis R. W. (1977) Science 196:180; and Goodspeed et al. (1989) Gene 76: 1; each of which is incorporated herein by reference). Where a cDNA clone is desired, clone libraries containing cDNA derived from viral RNA or from RNA isolated from cells expressing viral polypeptides, are preferred. Alternatively, synthetic polynucleotide sequences corresponding to the desired viral sequences may be constructed by chemical synthesis of oligonucleotides.

Additionally, the polymerase chain reaction (PCR), using primers based on the known viral sequence, may be used to amplify DNA fragments from genomic DNA, mRNA pools, or from cDNA clone libraries. U.S. Pat. Nos. 4,683,195 and 4,683,202 describe the PCR method. Additionally, PCR methods employing one primer that is based on the known viral sequence and a second primer that is not based on the known viral sequence, may be used. For example, a second primer that is homologous to or complementary to a vector sequence or sequence external to the viral sequence, may be used.

It is apparent to one of skill in the art that nucleotide substitutions, deletions, and additions may be incorporated into the polynucleotides of the invention. Nucleotide sequence variation may result from sequence polymorphisms of alleles, minor sequencing errors, and the like of the polynucleotide encoding an anti-apoptotic polypeptide. However, such nucleotide substitutions, deletions, and additions should not substantially disrupt the ability of the polynucleotide to hybridize the known polynucleotide sequences, under hybridization conditions that are sufficiently stringent to result in specific hybridization.

Specific hybridization is defined herein as the formation of hybrids between a probe polynucleotide (e.g., a polynucleotide of the invention which may include substitutions, deletion, and/or additions) and a specific target polynucleotide (e.g., a polynucleotide of the invention, such as a polynucleotide encoding an anti-apoptotic polypeptide), wherein the probe preferentially hybridizes to the specific target such that, for example, a single band corresponding to one or more of the isoforms of an alternatively spliced mRNA species can be identified on a Northern blot of RNA prepared from a suitable cell source (e.g., cells expressing the anti-apoptotic polypeptide).

Polynucleotides of the invention and recombinantly produced polynucleotides, or analogs thereof, may be prepared on the basis of the sequence data, according to methods known in the art and described in Maniatis et al., Molecular Cloning: A Laboratory Manual, 2nd Ed., (1989). Cold Spring Harbor, N.Y. and Berger and Kimmel, Methods in Enzymology, Volume 152, Guide to Molecular Cloning Techniques (1987), Academic Press, Inc., San Diego, Calif.; each of which is incorporated herein by reference.

Polynucleotides of the invention may be short oligonucleotides (e.g., 15–200 bases long), such as for use as hybridization probes and PCR (or LCR) primers. Polynucleotide sequences of the invention may also comprise part of a larger polynucleotide (e.g., a cloning vector comprising a clone) and may be fused, by polynucleotide linkage, in frame with another polynucleotide sequence encoding a different polypeptide (e.g., glutathione S-transferase or β-galactosidase) for encoding expression of a fusion polypeptide. Typically, the polynucleotides of the invention comprise at least 25 consecutive nucleotides which are substantially identical to a naturally-occurring polynucleotide of the invention, more usually the polynucleotides of the invention comprise at least 50 to 100 consecutive nucleotides which are substantially identical to a naturally-occurring polynucleotide sequence encoding an anti-apoptotic polypeptide. However, it will be recognized by those of skill that the minimum length of a polynucleotide required for specific hybridization to a target sequence will depend on several factors: G/C content, positioning of mismatched bases (if any), degree of uniqueness of the sequence as compared to the population of target polynucleotides, and chemical nature of the polynucleotide (e.g., methylphosphonate backbone, phosphorothiolate, etc.), among others. Substantially identical means that the sequence of the polynucleotides of the instant invention is at least about 30%, more preferably about 45%, even more preferably about 65%, and most preferably about 80% identical to the sequence of the naturally-occurring polynucleotide.

If desired, PCR amplimers for amplifying substantially fulllength cDNA copies may be selected at the discretion of the practitioner. Similarly, amplimers to amplify single exons or portions of the particular polynucleotide of the invention may be selected.

Each of these sequences may be used as hybridization probes or PCR amplimers to detect the presence of a particular species of RNA, for example to diagnose a viral disease characterized by the presence of an elevated or reduced level of a particular species of RNA in, for example lymphocytes, or to perform tissue typing (i.e., identify tissues characterized by the expression of a particular species of RNA), and the like. The sequences may also be used for detecting genomic polynucleotide sequences in a DNA sample, such as for forensic DNA analysis (e.g., by RFLP analysis, PCR product length(s) distribution, etc.) or for diagnosis of diseases characterized by amplification and/or rearrangements of a particular gene.

Methods of Assaying for the Anti-apoptotic Activity of a Specific Viral Polypeptide Transiently Expressed in Mammalian Cells The anti-apoptotic activity of a specific polypeptide can be assayed for by transient expression in mammalian cells. Cells that transiently express a specific polypeptide are useful for characterizing the structural and functional properties of the polypeptide having anti-apoptotic activity, and also useful for characterizing the antiviral compounds that interact with or bind to the polypeptide and interfere with the anti-apoptotic activity of the polypeptide. For example, such an assay for detecting the anti-apoptotic activity of a specific viral polypeptide can be used to screen candidate antiviral compounds for their ability to interfere with the anti-apoptotic activity of a specific viral polypeptide and, thereby, induce or restore apoptosis. Further, the assay is useful in identifying and characterizing the functional domains of a specific polypeptide. For example, the specific polypeptide and polynucleotide sequence critical for anti-apoptotic activity or for intermolecular interactions of a specific polypeptide can be identified and characterized using such an assay. Moreover, the assay provides a method of identifying and characterizing the manner or region in which an antiviral compound interacts or binds to the viral polypeptide, under physiological conditions.

Figure 8A:
FIGS. 8A and B are histograms that demonstrate the anti-apoptotic activity of pUL36 and $pUL37_S$ in HeLa cells transfected with mammalian transient expression vectors coding individually for pUL36 and $pUL37_S$, respectively, and treated with anti-Fas and cycloheximide (CHX).
Figure 8B:
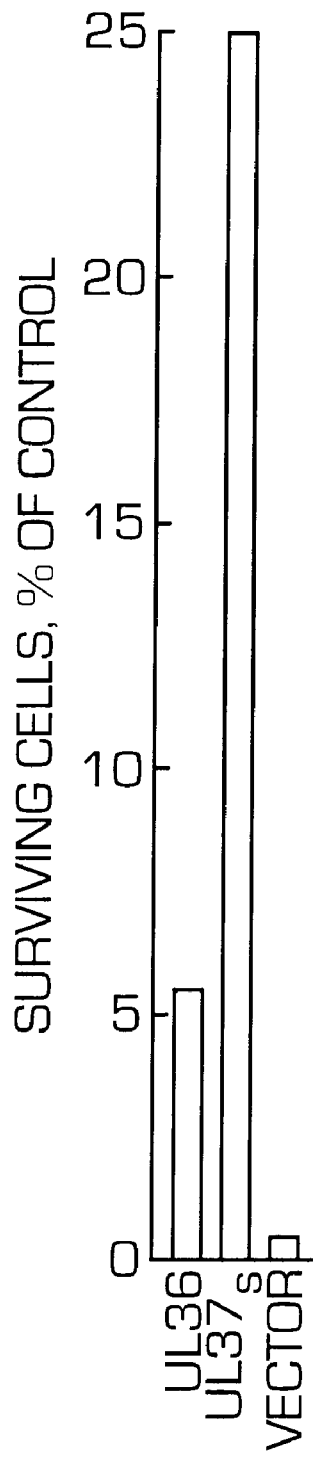

In a preferred embodiment, the anti-apoptotic activity of HCMV polypeptides pUL37$_S$ and pUL36 (including any unspliced and alternatively spliced variants of the polypeptide encoded by UL36) is confirmed by generating, individually, the regions of DNA closely covering the ORFs by PCR, ligating the PCR-generated fragment into the expression vector pCR3.1-uni, sequencing the cloned polynucleotide fragment, and testing the clone for anti-apoptotic activity in HeLa cells. Using this approach, the present inventors demonstrated that genomic sequences covering ORF UL37$_S$ or ORF UL36 protect HeLa cells against anti-Fas-induced apoptosis (FIG. 8). Further, the anti-apoptotic activity of any other polypeptides that may be encoded by the UL36 region, defined by nucleotides 49,776–48,246 on the HCMV AD169 genome, may be identified using this same approach.

Figure 9:
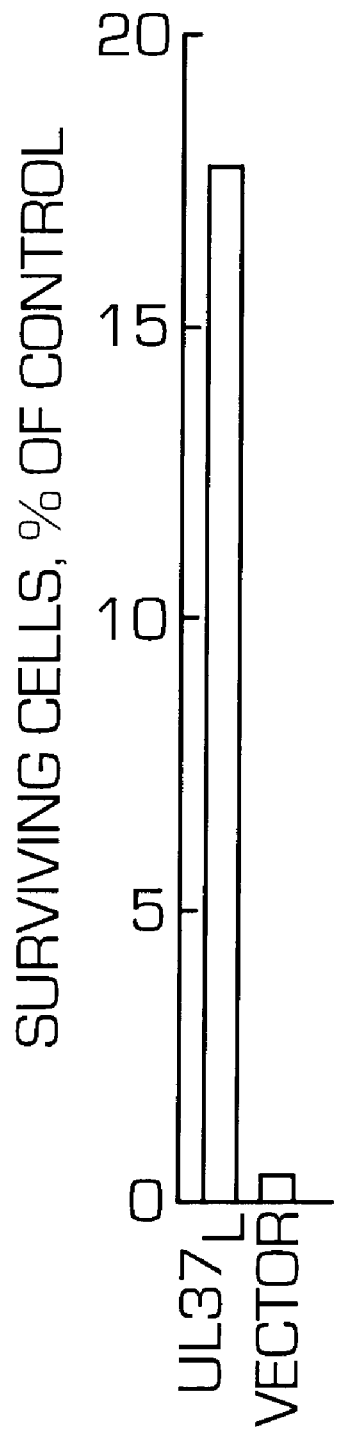
FIG. 9 is a histogram that demonstrates the detection of the anti-apoptotic activity of $pUL37_L$ in HeLa cells transfected with a mammalian transient expression plasmid coding for $pUL37_L$ and treated with anti-Fas and cycloheximide (CHX).

In another preferred embodiment, the DNA covering ORF of PUL37$_L$ is generated by PCR from a cDNA library made from HCMV-infected cells, ligated into an expression vector, sequenced, and the clone tested for anti-apoptotic activity in HeLa cells. The cDNA rather than genomic DNA is used to express pUL37$_L$ in order to prevent the expression of pUL37$_S$. Using this approach, the present inventors demonstrated that pUL37$_L$ is also anti-apoptotic (FIG. 9).

Methods of Assaying for the Anti-apoptotic Activity of a Specific Viral Polypeptide Stably Expressed in Mammalian Cells The anti-apoptotic activity of a specific polypeptide can be assayed for in mammalian cells stably transformed with a polynucleotide specifically encoding the polypeptide. A stably transformed cell line that continuously expresses the specific polypeptide is useful for characterizing the structural and functional properties of the polypeptide having anti-apoptotic activity, and also useful for characterizing the antiviral compounds that interact with or bind to the polypeptide and interfere with the anti-apoptotic activity of the polypeptide. For example, the assay is useful in identifying and characterizing the functional domains of a specific polypeptide. Also, the specific polypeptide and polynucleotide sequence critical for anti-apoptotic activity or for intermolecular interactions of a specific polypeptide can be identified and characterized using such an assay. Moreover, such an assay for detecting the anti-apoptotic activity of a specific viral polypeptide can be used to screen candidate antiviral compounds for their ability to interfere with the anti-apoptotic activity of a specific viral polypeptide and, thereby, induce or restore apoptosis. Also, the assay provides a method of identifying and characterizing the manner or region in which an antiviral compound interacts or binds to the viral polypeptide, under physiological conditions.

Clones encoding a polypeptide, having anti-apoptotic activity, can be stably transfected into mammalian cells using standard protocols known to those skilled in the art (e.g., see Sambrook et al., 1989, which is incorporated herein by reference) or by using commercially available transfection kits such as those sold by Stratagene, La Jolla, Calif., or Qiagen, Valencia, Calif. Such clones generated by stable transfection can continuously (as opposed to transiently) express the encoded polypeptide. Positives, i.e., cells stably transfected, are selected in a medium containing a selection agent, for example G418 or puromycin, that permits only stably transfected cells to survive.

The surviving clones, for example G418 or puromycin resistant clones, are then screened for the expression of the encoded polypeptide and the positive cells expressing the encoded polypeptide are isolated and subcultured. As an example, the transfected cells can be screened for the expressed polypeptide by Western Blot analysis using antibody that recognizes the polypeptide. Further, cells stably transfected with a control polynucleotide not encoding a polypeptide having anti-apoptotic activity, can be used as a negative control in the detection of the expressed polypeptide, such as in a Western blot analysis, and in experiments studying the anti-apoptotic activity of the clones. An example of a control polynucleotide is an expression vector that does not carry an inserted polynucleotide encoding a polypeptide having anti-apoptotic activity.

In a preferred embodiment, HeLa clones continuously (as opposed to transiently) express the version of $pUL37_S$ tagged with the C-terminal myc-peptide (amino acids 408–421 within the carboxy terminal domain of human cMyc) generated by stable transfection with either an expression plasmid containing $UL37_S$ alone, or in a mixture with an expression plasmid coding for puromycin-N-acetyl-transferase such as pPUR (Clontech, Palo Alto, Calif.). Following the transfection, drug-resistant clones are selected in medium containing G418 (0.7 mg/mL) or in medium containing puromycin (1 µg/ml), and then the clones are screened for the expression of pUL36-myc-tagged and $pUL37_S$-myc-tagged polypeptides, respectively, by Western analysis with 9E10 anti-Myc antibody (Santa Cruz Biotechnology, Inc., Santa Cruz, Calif.). In using this approach, the present inventors isolated four clones that expressed $pUL37_S$-myc (designated as HeLa/$UL37_S$). These clones were then used to conduct further studies reported in Example 8. Also, four G418-resistant clones of HeLa cells stably transfected with the empty vector (pcDNA3/myc) were isolated by similar procedures, two with G418 (HeLa/G418) and two with puromycin (HeLa/puro), and used as a negative control in the Western blot analysis and experiments studying the anti-apoptotic activity of the clones.

The sensitivity of the HeLa/$pUL37_S$ towards Fas- and TNFR-1-mediated apoptosis was tested. The four clones of each type were tested and all displayed a similar degree of anti-apoptotic activity. Virtually none of the HeLa/$pUL37_S$ cells underwent apoptosis induced by anti-Fas or TNF-α, while virtually all control cells (transfected with the pCDNA3/myc) died.

Methods of Identifying Physiological Molecules that Specifically Bind to Viral Polypeptides Having Anti-apoptotic Activity Physiological molecules, such as polypeptides, polynucleotides, RNA, DNA, amino acids, and nucleic acids, specifically bind to viral polypeptides, having anti-apoptotic activity, and are potentially important apoptosis regulatory molecules. Such physiological molecules are also referred to herein as accessory molecules. Such accessory molecules may participate in the signalling or induction of apoptosis. Thus, the specific interaction of viral anti-apoptotic polypeptides with such molecules may prevent the molecule from functioning, thereby, interfering with apoptosis.

Methods identifying such physiological molecules that interact specifically with viral polypeptides having anti-apoptotic activity have utility in the development of compositions and methods of screening for antiviral compounds. For example, antiviral compounds that diminish the specific binding of physiological molecules to viral polypeptides having anti-apoptotic activity could interfere with such activity and, thereby, induce or restore apoptosis.

Further, the identification and analysis of such physiological molecules is facilitated by the use of fragments of the viral polypeptides having anti-apoptotic activity. For example, a specific portion or fragment of the viral polypeptide having anti-apoptotic activity, such as a functional domain, may be used for screening for a physiological molecule that specifically binds to a specific sequence or domain of the viral polypeptide, and for characterizing the interaction of the physiological molecule with a specific sequence or domain of the viral polypeptide.

In addition, such viral polypeptides having anti-apoptotic activity may be modified using chemical methods or genetic engineering methods known in the art such as those described and referenced hereinbelow under Modifications of Polynucleotides and Polypeptides. As an example, the polypeptides may be modified by the attachment of linkers that join two or more of the viral polypeptides, for the purposes of screening for and characterizing such physiological molecules. For example, two or more of the viral polypeptides having anti-apoptotic activity may be joined together by a peptide linker. As another example, the polypeptides may be modified by means of genetic engineering so that two or more of the polypeptides are joined together when expressed as a fusion polypeptide.

An embodiment is a method of identifying physiological molecules that specifically bind to viral polypeptides having anti-apoptotic activity. In addition, such viral polypeptides having anti-apoptotic activity may be modified using chemical methods or genetic engineering methods known in the art such as those described and referenced hereinbelow under Modifications of Polynucleotides and Polypeptides.

Another embodiment is a method of identifying physiological molecules that specifically bind to HCMV polypeptides having anti-apoptotic activity. In addition, such HCMV polypeptides having anti-apoptotic activity may be modified using chemical methods or genetic engineering methods known in the art such as those described and referenced hereinbelow under Modifications of Polynucleotides and Polypeptides.

Another embodiment is a method of identifying physiological molecules that specifically bind to at least one of HCMV polypeptides pUL36 (including any unspliced and alternatively spliced variants of the polypeptide encoded by UL36), $pUL37_S$, and $pUL37_L$. In addition, such HCMV polypeptides may be modified using chemical methods or genetic engineering methods known in the art such as those described and referenced hereinbelow under Modifications of Polynucleotides and Polypeptides.

A preferred embodiment is a method of identifying polypeptides that specifically bind to at least one of HCMV polypeptides pUL36, $pUL37_S$, and $pUL37_L$. In addition, such HCMV polypeptides may be modified using chemical methods or genetic engineering methods known in the art such as those described and referenced hereinbelow under Modifications of Polynucleotides and Polypeptides.

Another embodiment is a method of identifying amino acids that specifically bind to at least one of HCMV pUL36, $pUL37_S$, and $pUL37_L$. In addition, such HCMV polypeptides may be modified using chemical methods or genetic engineering methods known in the art such as those described and referenced hereinbelow under Modifications of Polynucleotides and Polypeptides.

An embodiment is a method of identifying polynucleotides, including DNA and RNA, that specifically bind to at least one of HCMV polypeptides pUL36, $pUL37_S$, and $pUL37_L$. In addition, such HCMV polypeptides may be modified using chemical methods or genetic engineering methods known in the art such as those described and referenced hereinbelow under Modifications of Polynucleotides and Polypeptides.

An embodiment is a method of identifying nucleic acids that specifically bind to at least one of HCMV polypeptides pUL36, $pUL37_S$, and $pUL37_L$. In addition, such HCMV polypeptides may be modified using chemical methods or genetic engineering methods known in the art such as those described and referenced hereinbelow under Modifications of Polynucleotides and Polypeptides.

A preferred method of isolating a physiological molecule that specifically binds to a viral polypeptide having anti-apoptotic activity is by contacting the viral polypeptide in a cell extract to an affinity tag, such as an antibody, that binds to the viral polypeptide, and isolating the resultant immune complexes. For example, at least one of HCMV polypeptides pUL36, $pUL37_S$, and $pUL37_L$ can be contacted in a cell extract to an antibody that binds, respectively, to at least one of the HCMV polypeptides, and the resultant immune complexes isolated. Other molecules, such as derivatives of avidin or biotin, that bind to at least one of the HCMV polypeptides, may be used as an affinity tag. In addition, such HCMV polypeptides may be modified using chemical methods or genetic engineering methods known in the art such as those described and referenced hereinbelow under Modifications of Polynucleotides and Polypeptides.

The isolated immune complexes may contain an accessory molecule, such as a polypeptide or polynucleotide, bound to the viral polypeptide having anti-apoptotic activity. The bound accessory molecule may be identified and isolated by its displacement from the immune complexes with either a denaturing agent or other standard methods (e.g., see Current Protocols in Molecular Biology on CD-ROM, John Wiley & Sons, Inc., 1998, which is incorporated herein by reference). Other standard methods for freeing and isolating the bound accessory molecule include the use of a displacing reagent such as a solution of inorganic or organic electrolytes at low or high concentrations and at different pH values, or a chaotropic agent.

In the case where the physiological molecule is a polypeptide, preferably the denaturing agent is a reducing agent. The denatured and preferably reduced polypeptides can then be resolved electrophorectically on a polyacrylamide gel. The putative accessory polypeptides can be identified on the polyacrylamide gel by one or more of various well known methods (e.g., Coomassie staining, Western blotting, silver staining, etc.), and isolated by resection of a portion of the polyacrylamide gel containing the relevant identified polypeptide, and elution of the polypeptide from the gel portion.

As an example of freeing and isolating the accessory molecule, the inventors lysed and then treated cells that had continuously expressed $pUL37_S$myc (HeLa/$UL37_S$) with anti-myc antibody. The immunonocomplexes were then collected with protein G agarose affinity beads and then analyzed by sodium dodecyl sulfate polyacrylamide gel electrophoresis (SDS-PAGE). Polypeptide bands on the gel were visualized by silver-stain. HeLa/pcDNA3 were used as a control. At least two polypeptide bands of the HeLa/$UL37_S$ immunocomplexes were visualized on the gel that were not present in the HeLa/pcDNA3 immunocomplexes. The apparent sizes of these two bands correspond to approximately 115 kDa and 145 kDa. The two polypeptides in these two bands could then be isolated from the polyacrylamide gel and their amino acid sequences (total or partial) determined by standard methods (e.g., see Current Protocols in Molecular Biology on CD-ROM, Chapter 10, John Wiley & Sons, Inc., 1998, which is incorporated herein by reference).

A yeast double-transformation assay (Chien et al. (1991) Proc. Natl. Acad. Sci. (U.S.A.) 88:9578, which is incorporated by reference) can be used to identify accessory polypeptides that specifically bind to viral polypeptides having anti-apoptotic activity, under physiological conditions. For example, the double-transformation assay can be used to identify accessory polypeptides that specifically bind to at least one of HCMV polypeptides pUL36, $pUL37_S$, and $pUL37_L$, under physiological conditions, forming an intermolecular polypeptide complex. In addition, such HCMV polypeptides may be modified using chemical methods or genetic engineering methods known in the art such as those described and referenced hereinbelow under Modifications of Polynucleotides and Polypeptides.

In a preferred embodiment, the GAL4 fusion polypeptide comprises a HCMV polypeptide having anti-apoptotic activity, such as pUL36, $pUL37_S$, and $pUL37_L$. In addition, such HCMV polypeptides having anti-apoptotic activity may be modified using chemical methods or genetic engineering methods known in the art such as those described and referenced hereinbelow under Modifications of Polynucleotides and Polypeptides. The other GAL 4 fusion polypeptide comprises a polypeptide encoded by a cDNA that is a member of a library, for example, a human cDNA library.

Alternatively, an *E. coli*/BCCP interactive screening system (Germino et al. (1993) Proc. Natl. Acad. Sci. (U.S.A.)

90:1639, which is incorporated herein by reference) can be used to identify the viral polypeptide binding sequences. Also, an expression library, such as the λgt11 cDNA expression library (Dunn et al. (1989) J. Biol. Chem. 264:13057, which is incorporated herein by reference), can be screened with a labelled viral anti-apoptotic polypeptide, such as HCMV polypeptide pUL36, pUL37$_S$, and pUL37$_L$, to identify cDNAs encoding polypeptides that specifically bind to such a viral polypeptide. In addition, such viral polypeptides having anti-apoptotic activity may be modified using chemical methods or genetic engineering methods known in the art such as those described and referenced hereinbelow under Modifications of Polynucleotides and Polypeptides.

For these procedures, cDNA libraries usually comprise mammalian cDNA populations, typically human, mouse, or rat and may represent cDNA produced from RNA and one cell type, tissue, or organ, and one or more developmental stage. Specific binding for screening cDNA expression libraries is usually provided by including one or more blocking agent (e.g., albumin, nonfat dry milk solids, etc.) prior to and/or concomitant with contacting the labeled viral anti-apoptotic polypeptide (and/or labeled antibody that recognizes such a viral polypeptide).

A putative accessory polypeptide may be identified as an accessory polypeptide by demonstration that the polypeptide binds to a viral polypeptide having anti-apoptotic activity. An example of such viral polypeptides include HCMV polypeptides pUL36, pUL37$_S$, and pUL37$_L$, and modified forms of such HCMV polypeptides. Such binding may be shown in vitro by various means, including, but not limited to, binding assays employing a putative accessory polypeptide that has been renatured subsequent to isolation by a polyacrylamide gel electrophoresis method.

Alternatively, binding assays employing recombinant or chemically synthesized putative accessory polypeptide may be isolated and all or part of its amino acid sequence determined by chemical sequencing, such as Edman degradation. The amino acid sequence information may be used to chemically synthesize the putative accessory polypeptide. The amino acid sequence may also be used to produce a recombinant putative accessory polypeptide by :1) isolating a cDNA clone encoding the putative accessory polypeptide by screening a cDNA library with degenerate oligonucleotide probes according to the amino acid sequence data, 2) expressing the cDNA in a host cell, and 3) isolating the putative accessory polypeptide.

Putative accessory polypeptides that bind viral anti-apoptotic polypeptides, such as HCMV polypeptides pUL36, pUL37$_S$, and pUL37$_L$, or modified forms of the polypeptides, in vitro, are identified as accessory polypeptides. Accessory polypeptides may also be identified by crosslinking in vivo with bifunctional crosslinking reagents (e.g., dimethylsuberimidate, glutaraldehyde, etc.), wherein the subsequent isolation of the crosslinked products includes the viral anti-apoptotic polypeptide. For a general discussion of cross-linking, see Kunkel et al. (1998) Mol. Cell. Biochem. 34:3, which is incorporated herein by reference. Preferably, the bifunctional crosslinking reagent will produce crosslinks which may be reversed under specific conditions after isolation of the crosslinked complex so as to facilitate isolations of the accessory polypeptide from the viral anti-apoptotic polypeptide. Isolations of crosslinked complexes that include a viral anti-apoptotic polypeptide are preferably accomplished by binding an antibody that binds the viral polypeptide with an affinity of at least $1\times10^7$ M$^{-1}$ to a population of crosslinked complexes and recovering only those complexes that bind to the antibody with an affinity of at least $1\times10^7$ M$^{-1}$. Polypeptides that are crosslinked to a viral anti-apoptotic polypeptide, such as pUL36, pUL37$_S$, and pUL37$_L$, are identified as accessory polypeptides.

Accordingly, screening assays can be developed for identifying candidate antiviral compounds that inhibit the binding of a viral anti-apoptotic polypeptide, such as pUL36, pUL37$_S$, and pUL37$_L$, to an accessory polypeptide under suitable binding conditions.

Similarly, screening assays can be developed for identifying putative accessory polynucleotides, including accessory DNA and RNA, that bind to viral anti-apoptotic polypeptides, such as pUL36, pUL37$_S$, and pUL37$_L$. These screening assays can be carrying out using standard procedures and assays described, for example, in: Current Protocols in Molecular Biology, John Wiley & Sons, Inc., 1995, F. M. Ausubel et al., eds, which is incorporated herein by reference. Moreover, such protein-DNA or protein-RNA interactions can be characterized, and the isolation of the specific polynucleotides that interact with the anti-apoptotic polypeptides can be performed using standard procedures and assays as described, for example, in: T. D. Levine et al., Mol. Cell. Biol. 13, 3494–3504, 1993; and L. M. Dember et al. , J. Biol. Chem. 271, 2783–2788, 1996; each of which is incorporated herein by reference.

Application of Antisense Polynucleotides

Additional embodiments directed to interfering with the expression of viral polynucleotides encoding polypeptides having anti-apoptotic activity, for example UL36 and UL37, include methods that employ specific antisense polynucleotides complementary to all or part of the sequences encoding the anti-apoptotic polypeptide, such as pUL36, pUL37$_S$, and PUL37$_L$. Such complementary antisense polynucleotides may include nucleotide substitutions, additions, deletions, or transpositions, so long as specific hybridization to the relevant target sequence corresponding to the sequences encoding the viral anti-apoptotic polypeptide is retained as a functional property of the polynucleotide. Complementary antisense polynucleotides include soluble antisense DNA or RNA oligonucleotides that can hybridize specifically to the viral RNA species and prevent or diminish transcription of the viral RNA species and/or translation of the encoded polypeptide (Ching et al. (1989) Proc. Natl. Acad. Sci. U.S.A. 86:10006; Broder et al. (1990) FEBS Letters 274:53; Holcenberg et al. WO 91/11535; U.S. Ser. No. 07/530,165; WO91/09865; WO91/04753; WO90/13641; and EP386563; each of which is incorporated herein by reference).

The antisense polynucleotides therefore inhibit production of polypeptides having anti-apoptotic activity, such as pUL36, pUL37$_S$, and pUL37$_L$. Antisense polynucleotides that prevent transcription and/or translation of RNA corresponding to the anti-apoptotic polypeptides may inhibit anti-apoptotic activity and, thereby, induce or restore apoptosis. Antisense polynucleotides of various lengths may be produced, although such antisense polynucleotides typically comprise a sequence of approximately at least 25 consecutive nucleotides that are substantially identical to a naturally-occurring viral polynucleotide sequence encoding an anti-apoptotic polypeptide, such as the sequence of UL36 and UL37.

Antisense polynucleotides may comprise soluble, oligonucleotides that are administered to the external milieu, either in the culture medium in vitro or in the circulatory system or interstitial fluid in vivo. Soluble antisense polynucleotides present in the external milieu have been shown to gain access to the cytoplasm and inhibit translation of specific RNA species. In some embodiments the antisense polynucleotides comprise methylphosphonate moieties. For general methods relating to antisense polynucleotides, see Antisense RNA and DNA (1988), D. A. Melton, Ed., Cold Spring Harbor Laboratory, Cold Spring Harbor, N.Y.

Retroviral vectors expressing a portion of the UL36 or UL37 genes in the anti-sense orientation can be constructed and used to infect one portion of a cell population, e.g., MRC-5 cells. As a control, a similar retroviral vector containing an irrelevant DNA insert (i.e., any DNA insert that is not homologous to the HCMV UL36 or UL37 polynucleotide sequences and does not up- or down-regulate production of UL36 or UL37 mRNAs) can be used to infect a second portion of the same cell population. The cell populations can then be selected in the presence of a selection agent, e.g., G418. Cells surviving the selection, e.g., G418-resistant cells, have been successfully infected, indicating that the vector DNA was integrated into the genome of the cells. These cells are then exposed to virus, having anti-apoptotic activity, and tested for the development of apoptosis. The testing can be performed by any of the methods described for detecting cell death and/or apoptosis (for example, those reviewed in Sellers, J. R., Cook, S., and Goldmacher, V. S., J. Immunol. Meth. 172, 255–264 (1994) and references cited therein; Telford, W. G., King, L. E., and Fraker, PlJ., J. Immunol. Meth. 172, 1–16 (1994) and references cited therein; Apoptosis Techniques and Protocols, Poirier, J. (ed.), Humana Press, Totowa, N.J., 1997; each of which is incorporated herein by reference): 1) by examining the extent of DNA degradation; and 2) by detecting the cell surface expression of phosphatidylserine (FIG. 12).

Compositions and Methods of Identifying Novel Antiviral Compounds that Diminish the Specific Binding of a Physiological Molecule to Anti-apoptotic Polypeptides A basis of the present invention is the finding that anti-apoptotic polypeptides, such as pUL36, pUL37$_S$, and pUL37$_L$, can form a complex, under physiological conditions, with cellular polypeptides involved in the apoptosis signaling pathway. This finding indicates that the viral anti-apoptotic polypeptide can function as a modulator of apoptosis through such intermolecular interactions. Such functional modulation can serve to couple a signal transduction pathway, via the viral anti-apoptotic polypeptide, to an apoptosis regulatory polypeptide (e.g., FADD, FLICE, Caspase 3 (cpp32), Apaf-1, Bcl-x$_L$, Bak, ICE, Bax, and BNIP-3.) or other physiological molecule (e.g., polynucleotide recognized by the anti-apoptotic polypeptide) and, thereby, permit the viral polypeptide to interfere with or inhibit apoptosis.

Assays for detecting the ability of antiviral compounds to inhibit or diminish the binding of anti-apoptotic polypeptides to physiological molecules involved in the apoptosis signalling pathway, such as FADD, FLICE, Caspase 3 (cpp32), Apaf-1, Bcl-x$_L$, Bak, ICE, Bax, and BNIP-3, provide for facile high-throughput screening of agent banks (e.g., compound libraries, peptide libraries, and the like) to identify antagonists or agonists to the viral anti-apoptotic polypeptide or a physiological molecule that interacts with the viral polypeptide (e.g., FADD, FLICE, Caspase 3 (cpp32), Apaf-1, Bcl-x$_L$, Bak, ICE, Bax, BNIP-3, or polynucleotide recognized by the viral polypeptide). Such antagonists and agonists may interfere with the anti-apoptotic activity of the viral polypeptides and, thereby, regulate apoptosis, e.g., induce or restore apoptosis in virally-infected cells and prevent viral replication. Thus, such compositions are useful in the treatment of viral diseases, and such methods are useful for screening for antiviral compounds, and may comprise, e.g., polypeptide, polynucleotide, amino acid, nucleic acid, and chemical compositions.

Administration of an efficacious dose of an compound capable of specifically inhibiting complex formation between the anti-apoptotic polypeptide and physiological molecule, (i.e., the intermolecular interaction or binding between the viral anti-apoptotic polypeptide and a physiological molecule involved in the apoptosis signalling pathway) to a patient can be used as a therapeutic or prophylactic method for treating pathological conditions (e.g., CMV mononucleosis; congenital CMV infection which may cause fetus abnormalities; CMV infection in the immunocompromised host, such as AIDS patients, bone marrow transplant recipients, organ transplant recipients which frequently results in CMV hepatitis; CMV pneumonitis; CMV esophagitis; CMV colitis; CMV retinitis; CMV disseminated disease, which is often fatal) which are effectively treated by interfering with or inhibiting anti-apoptotic activity and, thereby, inducing or restoring apoptosis and preventing viral replication.

In vitro polypeptide binding assays generally take one of two forms: immobilized anti-apoptotic polypeptides can be used to bind to labeled physiological molecule, e.g., a cellular polypeptide, or conversely, the immobilized physiological molecule, e.g., a cellular polypeptide, can be used to bind labeled anti-apoptotic polypeptides. In addition to these examples, there are many other types of binding assays, including the detection of the binding of two unlabeled molecules (e.g., polypeptides) using Biacore technology (Biacore Inc., Piscataway, N.J.), or disruption of binding of two molecules (e.g., polypeptides) with a third molecule (e.g., a polypeptide) which competes with binding to one of the first two molecules (e.g., polypeptides).

Typically, a labeled polypeptide is contacted with an immobilized polypeptide under aqueous binding conditions and the extent of binding is determined by measuring the amount of immobilized labeled polypeptide. In each case, the labeled polypeptide is contacted with the immobilized polypeptide under aqueous conditions that permit specific binding of the polypeptides to form a specific intermolecular complex, in the absence of added agent. Particular aqueous conditions may be selected by the practitioner according to conventional methods. For general guidance, the following buffered aqueous conditions may be used: 10–250 mM NaCl, 5–50 mM Tris HCl, pH 5–8, with optional addition of divalent cation(s) and/or metal chelators and/or nonionic detergents and/or membrane fractions. It is appreciated by those in the art that additions, deletions, modifications (such as pH) and substitutions (such as KCl substituting for NaCl or buffer substitution) may be made to these basic conditions. Modifications can be made to the basic binding reaction conditions so long as specific binding of anti-apoptotic polypeptides to physiological molecules, e.g., cellular polypeptides, occurs in the control reaction(s). Conditions that do not permit specific binding in control reactions (no agent included) are not suitable for use in binding assays.

Preferably, at least one polypeptide species is labeled with a detectable marker. Suitable labeling includes, but is not limited to, radiolabeling by incorporation of a radiolabeled amino acid (e.g., $^4$C-labeled leucine, $^3$H-labeled glycine, $^{35}$S-labeled methionine), radiolabeling by post-translational radioiodination with $^{125}$I or $^{131}$I (e.g., Bolton-Hunter reaction and chloramine T), labeling by post-translational phosphorylation with $^{32}$P (e.g., phosphorylase and inorganic radiolabeled phosphate) fluorescent labeling by incorporation of a fluorescent label (e.g., fluorescein or rhodamine), or labeling by other conventional methods known in the art. In embodiments where one of the polypeptide species is immobilized by linkage to a substrate, the other polypeptide is generally labeled with a detectable marker.

Additionally, in some embodiments an anti-apoptotic polypeptide may be used in combination with an accessory polypeptide (e.g., a cellular polypeptide which forms a complex with the anti-apoptotic polypeptide, in vivo), it is preferred that different labels are used for each polypeptide species, so that binding of individual and/or heterodimeric and/or multimeric complexes can be distinguished. For example, but not for limitation, an anti-apoptotic polypeptide, such as pUL36, pUL37$_S$, or pUL37$_L$, may be labeled with fluorescein and an accessory polypeptide, such as FADD, FLICE, Caspase 3 (cpp32), Apaf-1, Bcl-x$_L$, Bak, ICE, Bax, or BNIP-3, may be labeled with a fluorescent marker that fluoresces with either a different excitation wave-length or emission wavelength, or both. Alternatively, double-label scintillation counting may be used, wherein an anti-apoptotic polypeptide, is labeled with one isotope (e.g., $^3$H) and a second polypeptide species (e.g., FADD, FLICE, Caspase 3 (cpp32), Apaf-1, Bcl-x$_L$, Bak, ICE, Bax, or BNIP-3.) is labeled with a different iso-tope (e.g., $^{14}$C) that can be distinguished by scintillation counting using discrimination techniques.

Labeled polypeptide(s) are contacted with immobilized polypeptide(s) under aqueous conditions as described herein. The time and temperature of incubation of a binding reaction may be varied, so long as the selected conditions permit specific binding to occur in a control reaction where no agent is present. Preferable embodiments employ a reaction temperature of about at least 15 degrees Centigrade, more preferably 35 to 42 degrees Centigrade, and a time of incubation of approximately at least 15 seconds, although longer incubation periods are preferable so that, in some embodiments, a binding equilibrium is attained. Binding kinetics and the thermodynamic stability of heterodimer complexes determine the latitude available for varying the time, temperature, salt, pH, and other reaction conditions. However, for any particular embodiment, desired binding reaction conditions can be calibrated readily by the practitioner using conventional methods in the art, which may include binding analysis using Scatchard analysis, Hill analysis, and other methods (Proteins, Structures and Molecular Principles, (1984) Creighton (ed.), W. H. Freeman and Company. New York).

Specific binding of the labeled polypeptide (e.g., FADD, FLICE, Caspase 3 (cpp32), Apaf-1, Bcl-x$_L$, Bak, ICE, Bax, or BNIP-3.) to the immobilized polypeptide (e.g., an anti-apoptotic polypeptide), is determined by including unlabeled competitor polypeptide(s) (e.g., albumin). After a binding reaction is completed, labeled polypeptide(s) that is/are specifically bound to immobilized polypeptide is detected. For example and not for limitation, after a suitable incubation period for binding, the aqueous phase containing non-immobilized polypeptide is removed and the substrate containing the immobilized polypeptide species and any labeled polypeptide bound to it is washed with a suitable buffer, optionally containing unlabeled blocking agents), and the wash buffer(s) removed. After washing, the amount of detectable label remaining specifically bound to the immobilized polypeptide is determined (e.g., by optical, enzymatic. autoradiographic, or other radiochemical methods).

In some embodiments, addition of unlabeled blocking agents that inhibit non-specific binding are included. Examples of such blocking agents include, but are not limited to, the following: calf thymus DNA, salmon sperm DNA, yeast RNA, mixed sequence (random or pseudorandom sequence) oligonucleotides of various lengths, bovine serum albumin, nonionic detergents (NP-40, Tween, Triton X-100, etc.), nonfat dry milk proteins, Denhardt's reagent, polyvinylpyrrolidone, Ficoll, and other blocking agents. Practitioners may, in their discretion, select blocking agents at suitable concentrations to be included in binding assays. However, reaction conditions are selected so as to permit specific binding between an anti-apoptotic polypeptide, and a physiological molecule, in a control binding reaction. Blocking agents are included to inhibit nonspecific binding of labeled protein to immobilized polypeptide and/or to inhibit nonspecific binding of labeled polypeptide to the immobilization substrate.

In embodiments where a polypeptide is immobilized, covalent or noncovalent linkage to a substrate may be used. Covalent linkage chemistries include, but are not limited to, well-characterized methods known in the art (Kadonaga and Tijan (1986) Proc. Natl. Acad. Sci. (U.S.A.) 83:5889). One example, not for limitation, is covalent linkage to a substrate derivatized with cyanogen bromide (such as CNBr-derivatized Sepharose 4B). It may be desirable to use a spacer to reduce potential steric hindrance from the substrate. Noncovalent bonding of polypeptides to a substrate includes, but is not limited to, bonding of the polypeptide to a charged surface and binding with specific antibodies.

In one class of embodiments, parallel binding reactions are conducted, wherein one set of reactions serves as control and at least one other set of reactions includes various quantities of agents, mixtures of agents, or biological extracts, that are being tested for the capacity to inhibit binding of an anti-apoptotic polypeptide to a cellular polypeptide.

A preferred embodiment is a method of identifying antiviral compounds that diminish the specific binding of a physiological molecule to an HCMV polypeptide having anti-apoptotic activity, using an in vitro binding assay.

Another preferred embodiment is a method of identifying antiviral compounds that diminish the specific binding of a physiological molecule to at least one of pUL36, pUL37$_S$, and pUL37$_L$, using an in vitro binding assay. Such physiological molecules comprise polypeptide, polynucleotide, DNA, RNA, amino acid, and nucleic acid molecules.

Another preferred embodiment is a method of identifying antiviral compounds that diminish the specific binding of a cellular polypeptide, involved in the apoptosis signalling pathway, to at least one of pUL36, pUL37$_S$, and pUL37$_L$, using an in vitro binding assay.

Another preferred embodiment is a method of identifying antiviral compounds that diminish the specific binding of FADD, FLICE, Caspase 3 (cpp32), Apaf-1, Bcl-x$_L$, Bak, ICE, Bax, or BNIP-3 to at least one of pUL36, pUL37$_S$, and pUL37$_L$, using an in vitro binding assay.

Another preferred embodiment is a method of identifying antiviral compounds that diminish the specific binding of a cellular polynucleotide, such as a cellular DNA or RNA, to at least one of pUL36, pUL37$_S$, and pUL37$_L$, using an in vitro binding assay.

Screening assays can be developed for identifying antiviral compounds (e.g., polypeptides, polynucleotides including DNA and RNA, amino acids, nucleic acids, and chemical compounds) that diminish the specific binding of a physiological molecule (e.g., a polypeptide, polynucleotide, amino acid, or nucleic acid) to a viral anti-apoptotic polypeptide, such as pUL36, pUL37$_S$, or pUL37$_L$. These screening assays can be carried out using standard procedures and assays described, for example, in: Current Protocols in Molecular Biology, John Wiley & Sons, Inc., 1995, F. M. Ausubel et al., eds, which is incorporated herein by reference.

Numerous biochemical assays have been developed to screen for molecules that disrupt specific polypeptide interactions (e.g., interactions of viral polypeptides having anti-apoptotic activity) with physiological molecules (e.g., polypeptides, polynucleotides, amino acids, and nucleic acids). Some of these assays are designed to be conducted in a multiwell plate format (e.g., a 96-well plate) and utilize the enzyme-linked immunosorbent assay (ELISA) for quantitation. For example, in one assay, 96-well microtiter plates are coated with an avidin derivative to which a biotinylated molecule (e.g., comprising a physiological molecule) is bound. A GST- or $His_6$-fusion polypeptide (e.g., comprising a viral polypeptide having anti-apoptotic activity that can interact with the biotinylated molecule is added in the presence or absence of test compounds (i.e., candidate antiviral compounds). The plates are incubated to allow binding and then unbound GST-fusion or $His_6$-fusion polypeptide is removed by washing. The amount of the fusion polypeptide specifically bound to the tethered molecule is determined by the ELISA using an anti-GST antibody or a poly-HIS-binding reagent conjugated to horse radish peroxidase. Compounds which block the interaction between the biotinylated molecule and the fusion polypeptide cause a decrease in the ELISA signal. Thus, a decrease in the ELISA signal is indicative of a diminution in the binding of the physiological molecule to the viral polypeptide having anti-apoptotic activity.

Moreover, the diminution of such binding activity by a putative antiviral compound can be characterized, and the isolation of such an antiviral compound can be performed using standard procedures and assays as described, for example, in: T. D. Levine et al., Mol. Cell. Biol. 13, 3494–3504, 1993; and L. M. Dember et al., J. Biol. Chem. 271, 2783–2788, 1996; each of which is incorporated herein by reference.

Methods of Identifying Novel Antiviral Compounds that Specifically Bind to Anti-apoptotic Polypeptides, in an In Vitro Binding Assay Antiviral compounds (e.g., polypeptides, polynucleotides, amino acids, nucleic acids, and chemical compounds) that specifically bind to viral polypeptides having anti-apoptotic activity may interfere with the anti-apoptotic function of the viral polypeptides and thereby lead to the induction of apoptosis, preventing or inhibiting viral replication. Such antiviral compounds may be identified in the same manner as described above for the identification of accessory polypeptides or polynucleotides that bind specifically to such viral polypeptides. In addition, such antiviral compounds may be identified by using the ELISA-based assay described above.

As an example, 96-well microtiter plates can be coated with an avidin derivative to which a biotinylated molecule (e.g., comprising a test compound) is bound. A GST- or $His_6$-fusion polypeptide (e.g., comprising a viral polypeptide having anti-apoptotic activity) is then added to the plates. The plates are incubated to allow binding and then unbound GST-fusion or $His_6$-fusion polypeptide is removed by washing. The amount of the fusion polypeptide specifically bound to the tethered molecule is determined by the ELISA using an anti-GST antibody or a poly-HIS-binding reagent conjugated to horse radish peroxidase. There is an increase the ELISA signal when the fusion polypeptide is bound to the tethered molecule. Thus, an increase in the ELISA signal is indicative of the binding of the test molecule to the viral polypeptide having anti-apoptotic activity.

Moreover, the binding activity of the putative antiviral compound can be characterized, and the isolation of such an antiviral compound can be performed using standard procedures and assays as described, for example, in: T. D. Levine et al., Mol. Cell. Biol. 13, 3494–3504, 1993; and L. M. Dember et al., J. Biol. Chem. 271, 2783–2788, 1996; each of which is incorporated herein by reference.

A preferred embodiment is a method of identifying antiviral compounds that specif ically bind to HCMV polypeptides having anti-apoptotic activity, or modified forms of such polypeptides, using an in vitro binding assay.

Another preferred embodiment is a method of identifying antiviral compounds that specif ically bind to HCMV polypeptides pUL36, $pUL37_S$, and $PUL37_L$, or modified forms of such polypeptides, using an in vitro binding assay.

Suitable candidate antiviral compounds may be identified by screening of various commercially available synthetic or semisynthetic and natural libraries which are widely available, or by rational drug design based on polypeptide sequence homologies, X-ray structures or any standard methods that identify molecules that are likely to bind to the viral polypeptide having anti-apoptotic activity based on the analysis of the structures of the polypeptide and the compound. For further details and references see below Methods in Rational Drug Design.

Compositions, and Methods of Identifying Novel Antiviral Compounds, that Specifically Bind to Viral Polypeptides Having Anti-apoptotic Activity in a Double-Transformation Assay The double-transformation assay is also called the "Two-Hybrid System," and permits the rapid screening of a large number of cellular polypeptides for the identification and isolation of polypeptides that bind specifically to a known polypeptide of interest, in vivo (S. Fields and O. K. Song, *Nature* 340:245–246, 1989, which is incorporated herein by reference). Further, the assay has been widely used in the study of intermolecular polypeptide interactions in cells. The assay merely relies on the ability of two polypeptides to bind to each other and is not reliant on detailed or specific knowledge of the polypeptide structure, function, or sequence identity. This intermolecular polypeptide interaction results in the reconstitution of a transcriptional activator and the induction of a reporter gene product, which is easily detected by standard, routine assays. The double-transformation assay not only permits the identification, but also the isolation of polypeptides that specifically interact with and bind to a known polypeptide of interest, such as pUL36, $pUL37_S$, and $pUL37_L$, in a particular cell type, such as B cells.

Detection of the binding of a candidate polypeptide with a known polypeptide is dependent on the restoration of a transcriptional activator, such as yeast GAL4. Many transcriptional activators, such as yeast GAL4, consist of two functional domains; a DNA-binding domain and an activation domain. The pool of polynucleotide molecules encoding polynucleotides that may potentially interact with the known polypeptide, and the polynucleotide encoding the known polypeptide itself, are inserted into separate vectors. One vector encodes the DNA-binding domain such that an inserted polynucleotide molecule is expressed as a hybrid polypeptide containing the DNA-binding domain. Whereas, another vector encodes the activation domain such that an inserted polynucleotide molecule is expressed as a hybrid polypeptide containing the activation domain.

As a preferred embodiment, an HCMV polynucleotide encoding at least one of pUL36, pUL37$_S$, and pUL37$_L$, is inserted into a vector containing the DNA-binding domain. Whereas, the pool of polynucleotide molecules encoding polypeptides that may potentially bind to at least one of pUL36, pUL37$_S$, and pUL37$_L$ ("HCMV polypeptides"), are inserted into a vector containing the activation domain ("candidate polypeptides"). Thus, the HCMV hybrid polypeptide contains the DNA-binding domain and the candidate hybrid polypeptides contain the activation domain. Consequently, under these conditions, when a candidate polypeptide binds to at least one of the HCMV polypeptides, the two hybrid polypeptides combine to reconstitute a functional GAL4 transcriptional activator that induces the expression of a reporter gene fused to a GAL4 binding site and carried in the host yeast strain. Such positive candidate polypeptides, that bind to at least one of the HCMV polypeptides, are then detected by assaying for expression of the reporter gene.

Using the double-transformation assay, positives can be easily identified and distinguished from negatives and, thus, a large number of polypeptides can be readily screened. The product of the reporter gene is easily detected by employing a variety of standard and routine assays, some including color indicators. An example of a reporter gene is lacZ. Consequently, when a HCMV-binding polypeptide binds to the viral polypeptide, to reconstitute a functional GAL4 transcriptional activator, this specific polypeptide interaction induces the expression of the lacZ reporter gene. The product of lacZ expression, beta-galactosidase, is then detected by the addition of the reagent X-gal which turns the yeast cell blue in color. Thus, a positive blue yeast cell, containing a candidate polypeptide that binds to at least one of the HCMV polypeptides, is easily identified and distinguished from a background of white yeast cells that do not contain polypeptides that bind to the HCMV polypeptides.

Further, kits for performing the double-transformation assays have been commercially available. The commercially available kits include all the necessary reagents, strains, and instructions for carrying out such reactions, and come complete with instructions and standardized conditions for carrying out the assay in a step-wise manner. For example, Clontech has been marketing kits containing all the necessary reagents and strains since 1993 (Clontech 1993/1994 catalogue). In addition, many laboratory manuals include the necessary protocols for transformation and expression.

The transformation and expression of a large number of polynucleotides is routine and requires only standard procedures. Further, it is entirely feasible to screen a large number of polypeptides, expressed from a large number of polynucleotides, for a specific activity, e.g., binding to HCMV polypeptides having anti-apoptotic activity. Such screening, identification, and isolation of polypeptides with the desired activity, can be accomplished using routine experimentation.

Further, in order to identify the polypeptides of a particular cell type, e.g., B-cell, that interact specifically with a known polypeptide, e.g., pUL36, pUL37$_S$, and pUL37$_L$, a cDNA library made from RNA of that particular cell type can be used. Such libraries, and kits for preparing such libraries, are also readily available from commercial sources.

For commercial libraries, the complexity is typically in the range of $1-5\times10^6$ (Clontech 1993/1994 catalogue). For example, see pages 18–33 of the 1993/1994 Clontech catalogue. In order to adequately cover this range of complexity, about $10^6$ transformants should be generated. The generation of $10^6$ transformants is easily achieved, since the typical frequency of double transformation of yeast is within the range of $10^3$ to $10^4$ transformants per 1 µg of plasmid DNA. Consequently, under these conditions, in order to screen $1-5\times10^6$ cDNA clones, only 100–500 µg of plasmid DNA is needed.

A preferred embodiment, is a method of identifying novel antiviral compounds that specifically bind to HCMV polypeptides having anti-apoptotic activity in a double-transformation assay.

Another preferred embodiment, is a method of identifying novel antiviral compounds that specifically bind to HCMV polypeptides pUL36, pUL37$_S$, and pUL37$_L$ in a double-transformation assay.

Compositions and Methods of Identifying Novel Antiviral Compounds that Interfere with Anti-apoptotic Activity in Cells and, Thereby, Induce Apoptosis As a preferred embodiment, a candidate antiviral compound can be screened for its ability to induce apoptosis (detected with any marker of apoptosis) in any HCMV-infected cell line. Such antiviral compounds can be screened in a human, mammalian or any other eukaryotic cell, including yeast, that expresses either pUL37$_S$, or pUL36 or another polypeptide that has a sequence motif or a similar functional domain, or a similar function. The cells expressing such polypeptides would then be treated with the candidate antiviral compound and challenged with an anti-Fas, Fas-ligand, TNF-α, or any other agent that activates the caspase signaling apoptotic pathway and, consequently, the induction or restoration of apoptosis, the activity assayed.

As another preferred embodiment, a candidate antiviral compound may be screened for its ability to inhibit the interaction of pUL37$_S$, pUL36, or any other polypeptide having an anti-apoptotic function or motif, with FADD, FLICE, Caspase 3 (cpp32), Apaf-1, Bcl-x$_L$, Bak, ICE, Bax, or BNIP-3, or any other polypeptide having an apoptotic function or motif. Screening for such interaction, e.g., intermolecular polypeptide interaction, may be performed using a variety of standard screening protocols including immuno-assays, double-transformation assays, assays inhibiting enzymatic activity of any caspase or a related enzyme, or any other protein binding assay described herein.

Suitable candidate antiviral compounds may be identified by screening of various commercially available synthetic or semisynthetic and natural libraries which are widely available, or by rational drug design based on polypeptide sequence homologies, X-ray structures or any standard methods that identify molecules that are likely to bind to the viral polypeptide having anti-apoptotic activity based on the analysis of the structures of the polypeptide and the compound. For further details and references see below Methods in Rational Drug Design.

Production and Application of Antibodies

Anti-apoptotic polypeptides or analogs thereof, may be used to immunize an animal for the production of specific antibodies. These antibodies may comprise a polyclonal antiserum or may comprise a monoclonal antibody produced by hybridoma cells. For general methods to prepare antibodies, see Antibodies: A Laboratory Manual, (1988) E. Harlow and D. Lane, Cold Spring Harbor Laboratory, Cold Spring Harbor, N.Y., which is incorporated herein by reference.

For example, but not for limitation, a recombinant-produced viral polypeptide having anti-apoptotic activity, can be injected into a mouse along with an adjuvant following immunization protocols known to those of skill in the art so as to generate an immune response. Typically, approximately at least 1–50 μg of a polypeptide or analog is used for the initial immunization, depending upon the length of the polypeptide. Alternatively or in combination with a recombinantly produced polypeptide, a chemically synthesized peptide having a sequence of the viral polypeptide may be used as an immunogen to raise antibodies which bind to it. Immunoglobulins which bind the recombinant polypeptide with a binding affinity of at least $1 \times 10^7$ $M^{-1}$ can be harvested from the immunized animal as an antiserum, and may be further purified by immunoaffinity chromatography or other means. Additionally, spleen cells are harvested from the immunized animal (typically rat or mouse) and fused to myeloma cells to produce a bank of antibody-secreting hybridoma cells. The bank of hybridomas can be screened for clones that secrete immunoglobulins which bind the recombinantly produced polypeptide, or chemically synthesized polypeptide, with an affinity of at least $1 \times 10^6$ $M^{-1}$. Animals other than mice and rats may be used to raise antibodies; for example, goats, rabbits, sheep, and chickens may also be employed to raise antibodies reactive with a specific polypeptide. Transgenic mice having the capacity to produce substantially human antibodies also may be immunized and used for a source of antiserum and/or for making monoclonal secreting hybridomas.

Bacteriophage antibody display libraries may also be screened for binding to a specific polypeptide, for example pUL36, $pUL37_S$, or $pUL37_L$, or a fusion polypeptide comprising a polypeptide sequence of a particular epitope (generally at least 3–5 contiguous amino acids). Generally such polypeptides and the fusion polypeptide portions consisting of specific anti-apoptotic polypeptide sequences for screening antibody libraries comprise about at least 3 to 5 contiguous amino acids of a specific polypeptide, frequently at least 7 contiguous amino acids of the polypeptide, usually comprise at least 10 contiguous amino adds of the polypeptide, and most usually comprise a polypeptide sequence of at least 14 contiguous amino acids.

Combinatorial libraries of antibodies have been generated in bacteriophage lambda expression systems which may be screened as bacteriophage plaques or as colonies of lysogens (Huse et al. (1989) Science 246:1275; Caton and Koprowski (1990) Proc. Natl. Acad. Sci. (U.S.A.) 87:6450; Mullinax et al. (1990) Proc. Natl.

Acad. Sci. (U.S.A.) 87:8095; and Persson et al. (1991) Proc. Natl. Acad. Sci. (U.S.A.) 88:2432; each of which is incorporated herein by reference). Various embodiments of bacteriophage antibody display libraries and lambda phage expression libraries have been described (Kang et al. (1991) Proc. Natl. Acad. Sci. (U.S.A.) 88:4363; Clackson et al. (1991) Nature 352:624; McCafferty et al. (1990) Nature 348:552; Burton et al. (1991) Proc. Natl. Acad. Sci. (U.S.A.) 88:10134; Hoogenboom et al. (1991) NucleIc Acids Res. 19:4133; Chang et al. (1991) J. Immunol. 147:3610; Breitling et al. (1991) Gene 104:147; Marks et al. (1991) J. Mol. Biol. 222:581; Barbas et al. (1992) Proc. Natl. Acad. Sci. (U.S.A.) 89:4457; Hawkins and Winter (1992) J. Immunol. 22:867; Marks et at (1992) Biotechnology 10:779; Marks et al. (1992) J. Biol. Chem. 267:16007; Lowman et al (1991) Biochemistry 30:10832; Lerner et al. (1992) Science 258:1313; each of which is incorporated herein by reference). Typically, a bacteriophage antibody display library is screened with a polypeptide, such as a viral polypeptide having anti-apoptotic activity, that is immobilized (e.g., by covalent linkage to a chromatography resin to enrich for reactive phage by affinity chromatography) and/or labeled (e.g., to screen plaque or colony lifts).

Polypeptides which are useful as immunogens, for diagnostic detection of antibodies in a sample, for diagnostic detection and quantitation of an anti-apoptotic polypeptide in a sample (e.g., by standardized competitive ELISA), or for screening a bacteriophage antibody display library, are suitably obtained in substantially pure form, that is, typically about 50 percent (w/w) or more purity, substantially free of interfering proteins and contaminants. Preferably, these polypeptides are isolated or synthesized in a purity of at least 80 percent (w/w) and, more preferably, in at least about 95 percent (w/w) purity, being substantially free of other polypeptides of humans, mice, or other contaminants.

For some applications of these antibodies, such as identifying immunocrossreactive polypeptides, the desired antiserum or monoclonal antibody(ies) is/are not monospecific. In these instances, it may be preferable to use a synthetic or recombinant fragment of the full-length anti-apoptotic polypeptide as an antigen rather than using the full-length native polypeptide. More specifically, where the object is to identify immunocrossreactive polypeptides that comprise a particular structural moiety, such as a binding domain, it is preferable to use as an antigen a fragment corresponding to part or all of a commensurate structural domain in the anti-apoptotic polypeptide.

If an antiserum is raised to a fusion anti-apoptotic polypeptide, such as a fusion protein comprising immunogenic epitopes of a particular HCMV polypeptide, fused to β-galactosidase or glutathione S-transferase, the antiserum is preferably preadsorbed with the non-HCMV fusion partner (e.g., β-galactosidase or glutathione S-transferase) to deplete the antiserum of antibodies that react (i.e., specifically bind to) the non-HCMV portion of the fusion polypeptide that serves as the immunogen. Monoclonal or polyclonal antibodies which bind to the anti-apoptotic polypeptide can be used to detect the presence of such polypeptides in a sample, such as a Western blot of denatured polypeptides (e.g., a nitrocellulose blot of an SDS-PAGE) obtained from a cell extract, or from serum, tissue, or lymphocyte sample of a patient. Preferably quantitative detection is performed, such as by densitometric scanning and signal integration of a Western blot. The monoclonal or polyclonal antibodies will bind to the denatured anti-apoptotic polypeptide epitopes and may be identified visually or by other optical means with a labeled second antibody or labeled Staphylococcus aureus protein A by methods known in the art.

One use of such antibodies is to screen cDNA expression libraries, preferably containing cDNA derived from human or murine mRNA from various tissues, for identifying clones containing cDNA inserts which encode structurally-related, immunocrossreactive polypeptides, that are candidate anti-apoptotic-polypeptide-binding factors or anti-apoptotic-related polypeptides. Such screening of cDNA expression libraries is well known in the art, and is further described in Young et al., Proc. Natl. Acad. Sci. U.S.A. 80:1194–1198 (1983), which is incorporated herein by reference as well as other published sources. Another use of such antibodies is to identify and/or purify immunocrossreactive polypeptides that are structurally or evolutionarily related to the native anti-apoptotic polypeptide or to the corresponding anti-apoptotic polypeptide fragment (e.g., functional domain; binding domain) used to generate the antibody. The antibodies of the invention can be used to measure levels of a specific polypeptide in a cell or cell population, for example in a cell explant (e.g., lymphocyte sample) obtained from a patient. The antibodies can be used to measure the corresponding polypeptide level by various methods, including but not limited to: (1) standardized ELISA on cell extracts, (2) immunoprecipitation of cell extracts followed by polyacrylamide gel electrophoresis of the immunoprecipitated products and quantitative detection of the band(s) corresponding to the specific polypeptide, and (3) in situ detection by immunohistochemical staining with the antibodies and detection with a labeled second antibody. The measurement of the level of the specific polypeptide in a cell or cell population is informative regarding the apoptosis status of the cell or cell population.

Various other uses of such antibodies are to diagnose virally-induced diseases (e.g., CMV mononucleosis; congenital CMV infection which may cause fetus abnormalities; CMV infection in the immunocompromised host, such as AIDS patients, bone marrow transplant recipients, organ transplant recipients which frequently results in CMV hepatitis; CMV pneumonitis; CMV esophagitis; CMV colitis; CMV retinitis; CMV disseminated disease, which is often fatal), and for therapeutic application (e.g., as cationized antibodies or by targeted liposomal delivery) to treat such diseases, and the like.

A preferred embodiment is a polyclonal or monoclonal antibody that recognizes at least one of HCMV Polypeptides pUL36, pUL37$_S$, and pUL37$_L$.

Isolation and Synthesis of Polynucleotides and Polypeptides

The instant polynucleotides and polypeptides may be obtained as described herein, that is by recombinant means, or may be used to obtain homologous polynucleotides and polypeptides by hybridization, for example, an instant polynucleotide can be used as a probe of a gene bank or library to identify clones with suitable homology therewith.

Also, within the confines of available technology, the polynucleotides and polypeptides may be synthesized in vitro using, for example, solid phase oligonucleotide and oligopeptide synthetic methods known in the art. In particular, oligonucleotides, such as antisense oligonucleotides, can be synthesized on an Applied BioSystems oligonucleotide synthesizer according to specifications provided by the manufacturer.

Methods for PCR amplification are described in the art (PCR Technology: Principles and Applications for DNA Amplification ed. H. A. Erlich, Freeman Press, New York, N.Y. (1992); PCR Protocols: A Guide to Methods and Applications, eds. Innis, Gelfland, Snisky, and White, Academic Press, San Diego Calif. (1990); Mattila et al. (1991); Nucleic Acids Res. 19:4967; Eckert, K. A. and Kunkel, T. A. (1991); PCR Methods and Applications 1:17; PCR, eds. McPherson, Quirkes, and Taylor, IRL Press, Oxford; and U.S. Pat. No. 4,683,202; each of which is incorporated herein by reference).

Modification of Polynucleotides and Polypeptides

Modified polynucleotides and polypeptides are defined as those polynucleotides and polypeptides that, within the confines of available technology, may be chemically or genetically modified using chemical and genetic engineering methods known in the art. Examples of methods known in the art are, but not limited to, those described in Current Protocols in Molecular Biology, John Wiley & Sons, Inc., 1995, F. M. Ausubel et al., Eds.; Sambrook et al. Molecular Cloning: A Laboratory Manual, 2d ed. (1989) Cold spring harbor Laboratory Press, Cold Spring Harbor, N.Y.; and Proteins, Structures and Molecular Principles, (1984) Creighton (ed.), W. H. Freeman and Company, New York); each of which is incorporated herein by reference.

Relevant chemical modifications of polynucleotides include substitutions of normal phosphodiester bonds with one of the following types of bonds: 1) phosphotriester, methylphosphonate, phosphorothioate, as described in C. A. Stein and Y. C. Cheng, Science 261, 1004–1012, 1993 and incorporated herein by reference; 2) use of unnatural bases such as C-5 propynyl-2'-deoxyuridine or C-5 propynyl-2'-deoxycytidine; 3) use of unnatural sugars such as 2'fluororibose or 2'-O-methylribose, as described in R. W. Wagner, Nature 372, 333–335, 1994 and incorporated herein by reference; and 4) peptide nucleic acids (PNA) containing amide-containing backbones with nucleobases attached thereto, such as those described in Egholm, M., et al., J. Am. Chem. Soc. 114, 1895–1897, 1992; and Hyrup, B., et al., Bioorg. Med. Chem., 4, 5–23, 1996; each of which is incorporated herein by reference.

In particular, it may be advantageous to employ a peptide analog of pUL36, pUL37$_S$, or pUL37$_L$ as a pharmaceutical agent or as a commercial assay or research reagent. For example, a peptide analog of pUL36, pUL37$_S$, or pUL37$_L$, having high affinity for binding FADD, FLICE, Caspase 3 (cpp32), Apaf-1, Bcl-x$_L$, Bak, ICE, Bax, or BNIP-3 may be used as a competitive inhibitor of the intermolecular polypeptide complex formation by competing with native HCMV polypeptide for binding to FADD, FLICE, Caspase 3 (cpp32), Apaf-1, Bcl-x$_L$, Bak, ICE, Bax, or BNIP-3.

As an example, the HCMV polypeptides may be modified by the attachment of linkers that join two or more of the viral polypeptides together, for the purposes of screening for and characterizing physiological molecules that interact with such viral polypeptides. For example, two or more of the viral polypeptides having anti-apoptotic activity may be joined together by a peptide linker. As a further example, the polypeptides may be modified by means of genetic engineering so that two or more of the polypeptides are joined together when expressed as a fusion polypeptide.

Production and Application of Peptidomimetics

In addition to polypeptides consisting only of naturally-occurring amino acids, peptide analogs are also provided. Peptide analogs are commonly used in the pharmaceutical industry as non-peptide drugs with properties analogous to those of the template peptide. These types of non-peptide compounds are termed "peptide mimetics" or "peptidomimetics" (Fauchere, J. (1986) Adv. Drug Res. 15:29; Veber and Freidinger (1985) TINS p.392; and Evans et al. (1987) J. Med. Chem. 30:1229; each of which is incorporated herein by reference) and are usually developed with the aid of computerized molecular modeling.

Peptide mimetics that are structurally similar to therapeutically useful peptides may be used to produce an equivalent therapeutic or prophylactic effect. Generally, peptidomimetics are structurally similar to a paradigm polypeptide (i.e., a polypeptide that has a biochemical property or pharmacological activity), e.g., pUL36, pUL37$_S$, and pUL37$_L$, but have one or more peptide linkages optionally replaced by a linkage selected from the group consisting of: —CH$_2$NH—, —CH$_2$S—, —CH$_2$—CH$_2$—, —CH=CH— (cis and trans), —COCH$_2$—, —CH(OH)CH$_2$—, and —CH$_2$SO—, by methods known in the art and further described in the following references: Spatola, A. F. in "Chemistry and Biochemistry of Amino Acids, Peptides, and Proteins," B. Weinstein, eds., Marcel Dekker, New York, p.267 (1983); Spatola, A. G., Vega Data (March 1983), Vol. 1, Issue 3, "Peptide Backbone Modifications" (general review); Moreley, J. S., Trends Pharm. Sci. (1980) p.463–468 (general review); Hudson, D. et al., Int. J. Pept. Prot. Res. (1979) 14:177–185 (—CH$_2$NH—, CH$_2$CH$_2$—); Spatola, A. F. et al., Life Sci. (1986) 38:1243–1249 (—CH$_2$—S); Hann, M. M., J. Chem. Soc. Perkin Trans. I (1982) 307–314 (—CH—CH—, cis and trans); Almquist, R. G. et al., J. Med. Chem. (1980) 23:1392–1398 (—COCH$_2$—); Jennings-White, C. et al., Tetrahedron Lett. (1982) 23:2533(—

COCH$_2$); Szelke, M. et al., European Appln. EP 45665 (1982) CA: 97:39405 (1982) (—CH(OH)CH$_2$—); Holladay, M. W. et al., Tetrahedron Lett (1983) 24:4401–4404 (—C(OH)CH$_2$—); and Hruby, V. J., Life Sci. (1982) 31:189–199 (—CH$_2$—S—); each of which is incorporated herein by reference.

A particularly preferred non-peptide linkage is —CH$_2$NH—. Such peptide mimetics may have significant advantages over polypeptide embodiments, including, for example: more economical productions, greater chemical stability, enchanced pharmacological properties (half-life, absorption, potency, efficacy, etc.), altered specificity (e.g., a broad-spectrum of biological activities), reduced antigenicity, and others.

Labeling of peptidomimetics usually involves covalent attachment of one or more labels, directly or through a spacer (e.g., an amide group), to non-interfering position(s) on the peptidomimetic that are predicted by quantitative structure-activity data and/or molecular modeling. Such non-interfering positions generally are positions that do not form direct contacts with the macromolecules(s) to which the peptidomimetic binds to produce the therapeutic effect. Derivatization (e.g., labelling) of peptidomimetics should not abolish the desired biological or pharmacological activity of the peptidomimetic.

Systematic substitution of one or more amino acids of a consensus sequence with a D-amino acid of the same type (e.g., D-lysine in place of L-lysine) may be used to generate more stable peptides. In addition, constrained peptides comprising a consensus sequence or a substantially identical consensus sequence variation may be generated by methods known in the art (Rizo and Gierasch (1992) Ann. Rev. Biochem. 61:387, which is incorporated herein by reference); for example, by adding internal cysteine residues capable of forming intramolecular disulfide bridges which cyclize the peptide. Cyclic peptides comprising the sequence -WGR- and/or -QDN- and/or -FRDG- frequently are preferred.

The amino acid sequences of the HCMV polypeptides, pUL36, pUL37$_S$, and pUL37$_L$, identified herein will enable those of skill in the art to produce polypeptides corresponding to the HCMV polypeptide sequences and sequence variants thereof. Such polypeptides may be produced in prokaryotic or eukaryotic host cells by expression of polynucleotides encoding one of the HCMV polypeptide sequences identified herein, frequently as part of a larger polypeptide. Alternatively, such oligopeptides may be synthesized by chemical methods.

Methods for expression of heterologous polypeptides in recombinant hosts, chemical synthesis of polypeptides, and in vitro translation are well known in the art and are described further in Manitatis et al., Molecular Cloning: A Laboratory Manual (1989), 2nd Ed., Cold Spring Harbor N.Y.; Berger and Kimmel, Methods in Enzymology, Volume 152, Guide to Molecular Cloning Techniques (1987), Academic Press, Inc., San Diego, Calif.; Merrifield, J. (1969) J. Am. Chem. Soc. 91:501; Chaiken I. M. (1981) CRC Crit. Rev. Biochem. 11:255; Kaiser et al. (1989) Science 243:187; Merrifield, B. (1986) Science 232:342; Kent, S. B. H. (1988) Ann. Rev. Biochem. 57:957; and Offord, R. E. (1980) Semisynthetic Proteins, Wiley Publishing; each of which is incorporated herein by reference).

Peptides of a specific sequence can be produced typically by direct chemical synthesis, and used as antiviral compounds to competitively inhibit the interaction of pUL36, pUL37$_S$, and pUL37$_L$ with a physiological molecule that specifically binds to at least one of the HCMV polypeptides. Such synthetic peptides are frequently produced as modified peptides, with nonpeptide moieties attached by covalent linkage to the N-terminus and or C-terminus.

In certain preferred embodiments, either the carboxy-terminus or the amino-terminus, or both, are chemically modified. The most common modifications of the terminal amino and carboxyl groups are acetylation and amidation, respectively. Amino-terminal modifications such as acylation (e.g., actylation) or alkylations (e.g., methylation) and carboxy-terminal modifications such as amidation, as well as other terminal modifications, including cyclization, may be incorporated into various embodiments of the invention. Certain amino-terminal and/or carboxy-terminal modifications and/or peptide extensions to the core sequence can provide advantageous physical, chemical, biochemical, and pharmacological properties, such as: enhanced stability, increased potency and/or efficacy, resistance to serum proteases, desirable pharmacokinetic properties, and others. Such peptides may be used therapeutically to treat disease by interfering with the anti-apoptotic activity of viral polypeptides and/or regulating apoptosis in a cell population of a patient.

Methods of Rational Drug Design

HCMV polypeptides pUL36, pUL37$_S$, and pUL37$_L$, especially those portions of the HCMV polypeptides which form direct or specific contact with cellular polypeptides, such as FADD, FLICE, Caspase 3 (cpp32), Apaf-1, Bcl-x$_L$, Bak, ICE, Bax, and BNIP-3, can be used for the rational drug design of candidate antiviral drugs. Using the methods of the present invention to identify and isolate heterodimer complexes formed between one of the HCMV polypeptides and a specific cellular polypeptide, such as FADD, FLICE, Caspase 3 (cpp32), Apaf-1, Bcl-x$_L$, Bak, ICE, Bax, or BNIP-3, permits the production of substantially pure complexes and computational models that can be used for protein X-ray crystallography or other methods of structure analysis, such as the DOCK program (Kuntz et al. (1982) J. Mol. Biol. 161:269; and Kuntz I. D. (1992) Science 257:1078; each of which is incorporated herein by reference) and variants thereof. Potential therapeutic drugs may be designed rationally on the basis of structural information thus provided.

Thus, the present invention may be used to design drugs, including drugs with a capacity to interfere with the anti-apoptotic activity of viral polypeptides, by preventing the viral polypeptide having anti-apoptotic activity from specifically binding and forming a heterodimer complex with a physiological molecule and, thereby, induce or restore apoptosis in the host cells.

In one embodiment, such drugs are designed to prevent the formation of the heterodimer complex by preventing the viral polypeptide, having anti-apoptotic activity, from specifically binding to a physiological molecule such as a cellular polypeptide.

In a preferred embodiment, such drugs are designed to interfere with the anti-apoptotic activity of HCMV polypeptides and, thereby, induce or restore apoptotsis in the host cells. In particular, the drug would bind directly to the viral polypeptide and prevent it from forming a specific heterodimer complex with a physiological molecule such as a cellular polypeptide.

In another preferred embodiment, such drugs are designed to prevent at least one of the HCMV polypeptides pUL36, pUL37$_S$, and pUL37$_L$, from specifically binding to and forming a heterodimer complex with at least one of FADD, FLICE, Caspase 3 (cpp32), Apaf-1, Bcl-x$_L$, Bak, ICE, Bax, and BNIP-3.

As another preferred embodiment, an antiviral compound may be obtained by employing the rational design of a compound that would interfere with the anti-apoptotic activity of HCMV polypeptides pUL36, pUL37$_S$, and pUL37$_L$ and, thereby, induce or restore apoptosis in the host cells. The antiviral compound could interfere with the anti-apoptotic activity of such polypeptides by, for example, disrupting the specific binding of a physiological molecule with such polypeptides or could bind directly to the viral polypeptide and diminish the anti-apoptotic function of the polypeptide.

In one variation on the design, such drugs are structural mimics of the binding domain of the viral polypeptide, such as an HCMV polypeptide, having anti-apoptotic activity or the binding domain of a cellular polypeptide that specifically interacts with such a viral polypeptide.

As a preferred embodiment, a candidate antiviral compound may be obtained by employing the rational design of a compound that would be complementary to the structural domain of either pUL36, pUL37$_S$, or the domain of a cellular polypeptide having a domain that interacts with a HCMV anti-apoptotic polypeptide, and inhibits the specific interaction between the viral polypeptide and the cellular polypeptide.

The design of compounds that preferentially interact with and disrupt the formation or stability of the heterodimer complex formed between a viral polypeptide having anti-apoptotic activity and a polypeptide that specifically interacts with the viral polypeptide, can be developed using computer analysis of three dimensional structures. A set of molecular coordinates can be determined using: 1) crystallographic data, 2) data obtained by other physical methods, 3) data generated by computerized structure prediction programs operating on the deduced amino acid sequence data, or, preferably, a combination of these data. A preferred embodiment is the design of compounds that interact preferentially with a heterodimer complex formed between an HCMV polypeptide having anti-apoptotic activity and a cellular polypeptide that specifically interacts with the viral polypeptide, developed using computer analysis of three dimensional structures.

Another preferred embodiment is the design of compounds that interact preferentially with a heterodimer complex formed between any one of HCMV polypeptides pUL36, pUL37$_S$, and pUL37$_L$, and a cellular polypeptide, such as FADD, FLICE, Caspase 3 (cpp32), Apaf-1, Bcl-x$_L$, Bak, ICE, Bax, and BNIP-3, developed using computer analysis of three dimensional structures.

Examples of physical methods that may be used to define structure are, for example, two-dimensional homonuclear correlated spectroscopy (COSY). For those skilled in the art with one-dimensional NMR spectroscopy, COSY provides the kind of information available from a single-frequency decoupling experiment (e.g., which spins are scalar coupled to one another). In a COSY plot, the 1 dimensional spectrum lies along the diagonal, and the off-diagonal elements are present at the intersection of chemical shifts of groups that are J coupled. The "fingerprint" region contains ($^1$H$^N$, $^1$H$^\alpha$) cross-peaks from the peptide backbone. The degree of resolution of the "fingerprint" region of the COSY map obtained in H$_2$O is a good predictor of the success of sequencespecific assignments to be obtained without recourse to isotopic labeling.

Transferred nuclear Overhauser Effect (TRNOE) spectra ($^1$H NMR) relies on different two dimensional NOE spectra, and, in essence, looks at the conformation of the ligand just after it has dissociated from the polypeptide. The use of TRNOE presumes, however, that the bound and free ligands are in fast exchange on the chemical shift time scale, which translates to a ligand KD greater than or equal to about 1×10$^{-4}$ M. TRNOE methods are useful to crosscheck and augment the distance information obtained by other approaches.

It is not intended that the present invention be limited by the particular method used to obtain structural information. Furthermore, it is not intended that the present invention be limited to a search for any one type of drug; one or more of the compounds may be naturally-occurring or may be synthetic, or may be a chemically modified form of a naturally occurring molecule. In some embodiments, it is desirable to compare the structure of the viral polypeptides, having anti-apoptotic activity, such as the HCMV polypeptides pUL36, pUL37$_S$, and pUL37$_L$, to the structure(s) of other polypeptides. This structural comparison will aid in the identification of and selection of drugs that either selectively affect specific polypeptides, such as any one of pUL36, pUL37$_S$, and pUL37$_L$, or have a broad spectrum effect on more than one species of related polypeptide (e.g. other related anti-apoptotic viral polypeptides, in particular, other related anti-apoptotic HCMV polypeptides).

EXPERIMENTAL EXAMPLES

The invention will now be illustrated by reference to non-limiting examples. Unless otherwise stated, all percents, ratios, parts, etc. are by weight.

Example 1

This Example Demonstrates the Detection of Cell Death and Apoptosis.

Tumor necrosis factor receptor-1 (TNF-R1)-mediated apoptosis was induced by exposure of HeLa and MRC5 cells to TNF-α (10–60 ng/mL)+CHX (10–30 mg/mL). Fas-mediated apoptosis was induced by exposure of cells to an anti-Fas antibody (7C11 antibody at 10 to 60 ng/mL)+CHX (10–30 mg/mL). The degree of cell death was determined by visual scoring of cells under a phase microscope. A similar degree of cell death occurred when examined 20 to 28 h after the start of exposure. Further, a similar degree of cell death for a given reagent was produced when any concentration within the range indicated above was used.

The time-course of apoptosis was also analyzed by examining the expression of phosphatidylserine on the cell surface, as detected with FITC-labeled Annexin V, and by a dye-exclusion test using propidium iodide. These two tests were performed with an ApoAlert Annexin V Apoptosis kit (Clontech) in accordance with the manufacturer's recommendations, on a flow cytometer (FACScan, Becton-Dickinson).

DNA degradation in MRC-5 cells was examined as follows. 10$^6$ MRC-5 cells were either exposed for 12 h to anti-Fas in the presence of cycloheximide or not exposed (control). The cells were then resuspended by trypsinization, sedimented, and the pellet resuspended in 10 mL of lysis buffer (1% NP-40, 20 mM EDTA, 50 mM Tris.HCl, pH 7.5). After a 10 sec incubation at room temperature, the suspension was centrifuged in an Eppendorf centrifuge (5 min, 15,000 g), and the supernatant separated from the pellet and retained. Thereafter, the pellet was resuspended in 10 mL of the lysis buffer, centrifuged, and the resulting supernatant combined with the previously retained supernatant. Sodium dodecyl sulfate (at a final concentration of 1%), RNAse A (Sigma, at a final concentration of 5 mg/mL), and Proteinase K (Sigma, at a final concentration of 2.5 mg/mL) were then added to the combined supernatant, and the mixture incubated at 56° C., for 2 h. Ammonium acetate (at a final concentration of 2.5 M) and 2 volumes of ethanol were then added, mixed, and the mixture stored overnight, at −20° C. After the overnight precipitation, the DNA was sedimented by centrifugation in an Eppendorf centrifuge, for 30 min, at 14,000 rpm, then electrophoretically resolved on a 1% agarose gel, and visualized by ethidium bromide staining.

The degree of cell death in cells transfected with an indicator plasmid expressing E. coli β-galactosidase was determined by either a β-galactosidase ELISA (Boehringer Mannheim), in accordance with the manufacturer's recommendations, or by visually scoring, under a microscope, positive blue cells, expressing β-galacotosidase, after staining them with X-gal.

The degree of cell death in cells transfected with an indicator plasmid expressing Green Fluorescent Protein was determined by measuring the fraction of fluorescent cells in the total cell population, on a flow cytometer (FACScan, Becton-Dickinson).

Example 2

This Example Demonstrates the Detection of Anti-apoptosis Activity by Showing that HCMV Protects MRC-5 Fibroblasts Against Anti-Fas- and Anti-TNF-α-induced Apoptosis, and Provides a Method of Screening for Viral Targets having Anti-apoptotic Activity.

Two methods were used for the induction of apoptosis. The host cells were treated with anti-Fas antibodies or treated with tumor necrosis factor-α (TNF-α). Both methods of treatment activate the apoptotic signaling pathways involved in the elimination of virally-infected cells in the host animals (Mestan et al., 1986; Vilcek and Sen, 1996; Wong et al., 1986; Kagi et al., 1994; Sieg, et al., 1996; and Razvi and Welsh, 1995; each of which is incorporated herein by reference).

The present inventors then demonstrated that the infection of cells with HCMV prevents anti-Fas- and TNF-α-induced apoptosis. Protection of the host cells from apoptosis indicates that HCMV anti-apoptotic polypeptides prevent apoptosis induced by anti-Fas and TNF-α and, consequently, provides a method of screening for HCMV polynucleotides encoding polypeptides having anti-apoptotic activity.

These experiments were performed on MRC-5, a normal human fibroblast cell line which can be productively infected by HCMV in cell culture. MRC-5 cells readily undergo Fas- and TNF-R1-mediated apoptosis. FIG. 1A shows that MRC-5 cells died (disintegrated and then disappeared from the plate) within the first 24 h of their exposure to the anti-Fas monoclonal antibody 7C11, or to TNF-α as observed under a phase microscope. These reagents killed cells only in the presence of cycloheximide (CHX). CHX alone did not kill cells.

Anti-Fas-induced cell death of MRC-5 cells was also examined by a dye-exclusion test on a flow cytometer (FIG. 1B), and the results were consistent with those obtained by visual microscopic examination. Fas-mediated cell death was accompanied by the characteristic apoptotic events: 1) surface blebbing, as observed under a phase microscope (not shown); 2) emergence of phosphatidylserine, an early marker of apoptosis in the outer layer of the cell plasma membrane (FIG. 1C); 3) DNA degradation (not shown); and 4) protection by the caspase inhibitor Z-VADfmc (FIGS. 1A–C).

In the course of HCMV infection, the MRC-5 cells gradually developed resistance to TNF-R1 and Fas-mediated apoptosis. Although on day 0 and day 1 of infection, the cells were still sensitive to TNF-α- and anti-Fas-induced apoptosis, by day 2 most of the cells in the infected culture became insensitive to these stimuli, as was evident by microscopic examination of cell death (FIG. 2). The Flow-cytometric PI dye-exclusion test and the test for the surface expression of phosphatidylserine by apoptotic cells confirmed that a major fraction of HCMV-infected cells (72 h post-infection) retained their capacity to exclude the dye, and did not express phosphatidylserine following their exposure to anti-Fas+CHX (data not shown).

Example 3

This Example Demonstrates that Inhibitors of Viral Replication Diminish but do not Abolish the Induction of Resistance to Apoptosis in HCMV-infected Cells and that the Gene(s) Responsible for the Resistance to Apoptosis is Transcribed early in the Course of the Viral Replication.

The finding by the present inventors that MRC-5 cells become resistant to apoptosis only at a late stage of HCMV infection suggests that such resistance is mediated by: 1) a late HCMV gene; or 2) by an early or an immediate-early HCMV gene, the product of which accumulated to the level sufficient to protect cells from apoptosis only by day 2 of infection. To discriminate between these two mechanisms, MRC-5 cells were infected with HCMV in the presence (or absence) of inhibitors of viral DNA polymerase, such as phosphonoacetic acid or gancyclovir (Huang, 1975; Crumpacker, 1996) which prevent the expression of the late genes of HCMV in the host cell (Mocarski, 1996).

Figure 3A:
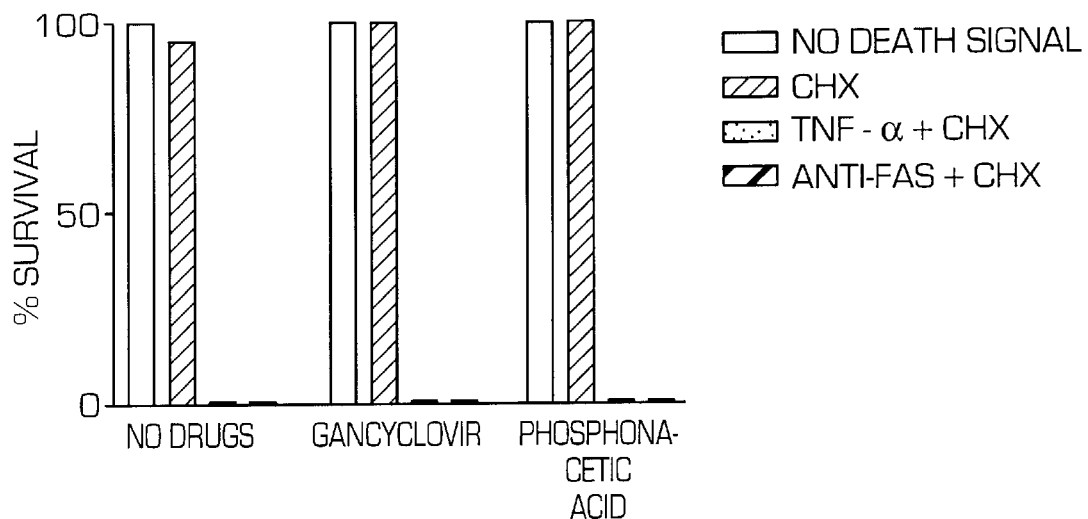
FIGS. 3A and B are histograms that show the effects of TNF-α and anti-Fas in the presence of cycloheximide (CHX) on the survival of MRC-5 fibroblasts infected with HCMV, and treated with gancyclovir or phosphonoacetic acid.
Figure 3B:
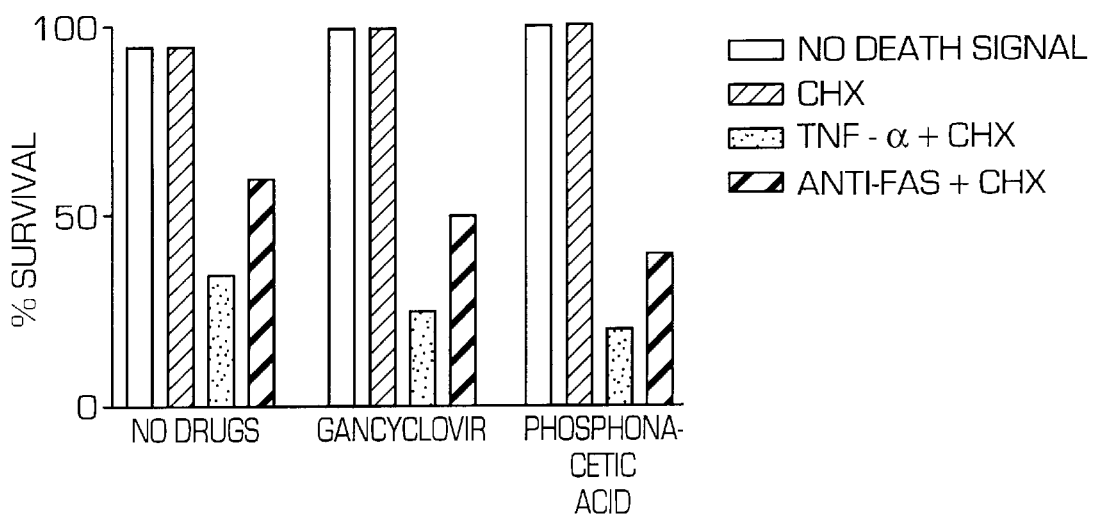
Figure 4B:
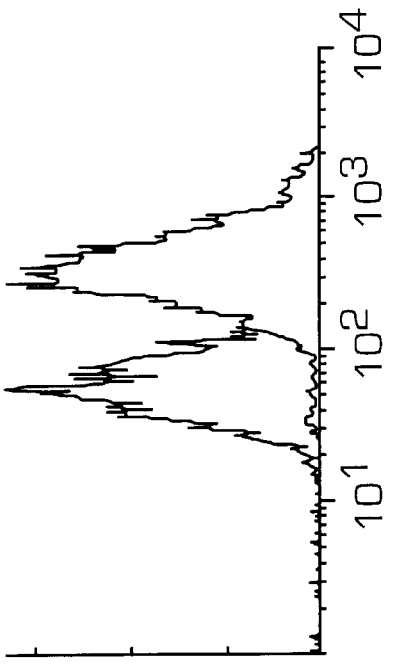
FIGS. 4A, B, C and D are measurements of cell fluorescence of MRC-5 cells that demonstrate the effect of HCMV infection on the cell surface expression of Fas.
Figure 4D:
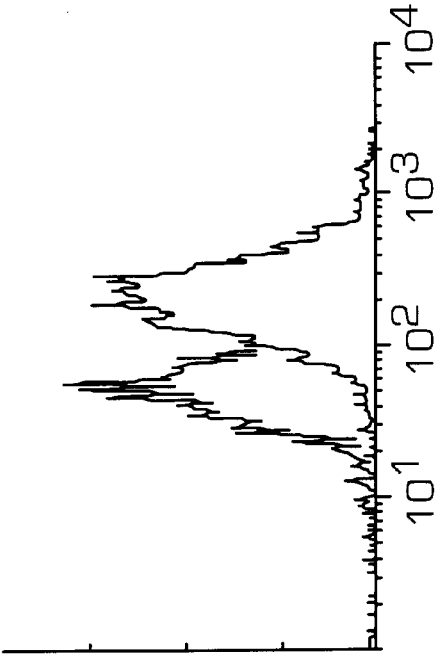
Figure 4A:
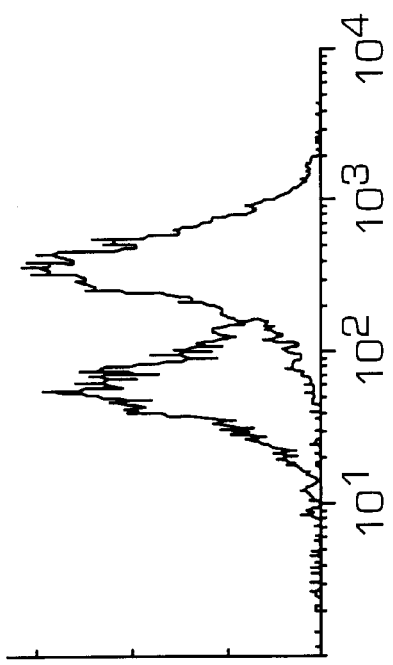
Figure 4C:
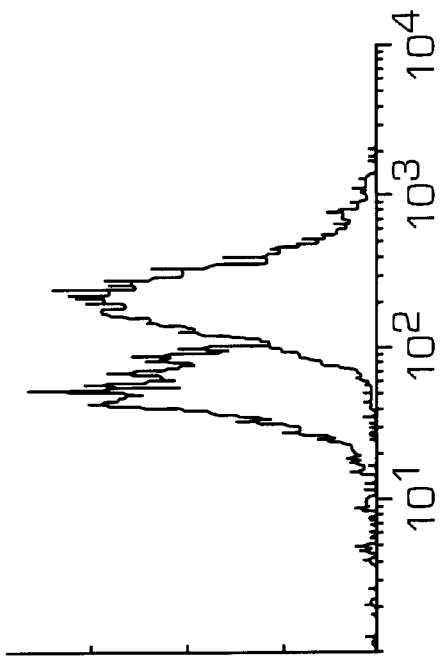

MRC-5 cells were infected with HCMV in the presence (or absence) of either phosphonoacetic acid or gancyclovir at a concentration sufficient to inhibit viral replication (Huang, 1975; Crumpacker, 1996). Two days later these cells were challenged with either anti-Fas+CHX or TNF-α+CHX (FIG. 3). Although nearly all non-infected MRC-5 cells underwent apoptosis, irrespective of the presence or absence of phosphonoacetic acid or gancyclovir, a major fraction of cells exposed to HCMV survived the challenge with the apoptotic stimuli in the absence of the viral DNA polymerase inhibitors. Further, a somewhat smaller but still large fraction of cells survived in the presence of the inhibitors. Thus, the insensitivity of HCMV-infected cells to apoptosis was not abolished by these drugs. These results indicate that the gene(s) responsible for this resistance to apoptosis is transcribed early in the course of the viral replication.

Example 4

This Example Demonstrates that the Infection of MRC-5 Fibroblasts with HCMV does not lead to the Disappearance of Fas from the Surface of Infected Cells.

HCMV-infected cells can become insensitive toward anti-Fas-induced apoptosis if the cells no longer express Fas on the cell surface, or if the expression of Fas in HCMV-infected cells is lost following exposure of the cells to CHX. However, the present inventors found that the infection of MRC-5 fibroblasts with HCMV does not lead to the disappearance of Fas from the surface of infected cells.

The expression of Fas on the surface of HCMV-infected cells treated or not treated with CHX was compared to those of 5 non-infected cells. The cells were incubated with anti-Fas or a negative control, a non-specific IgM, at 4° C., for 20 min, then with FITC-labeled anti-murine IgM antiserum, and cell-associated fluorescence was examined on a flow cytometer (FIG. 4). Expression of Fas antigen on the surface of HCMV-infected cells was only modestly diminished compared to that of non-infected MRC-5 cells. Further, CHX-treated cells did not differ in their Fas-expression from the respective non-CHX-treated cells.

Example 5

This Example Demonstrates that IE1 and IE2 do not Protect Cells Against Fas- and TNF-R1-mediated Apoptosis and that other HCMV Polypeptides are Responsible for the Resistance to Apoptosis.

It was previously reported that immediate early HCMV polypeptides IE1 and IE2 could protect HeLa cells against apoptosis induced by TNF-α or by a mutant adenovirus unable to express the E1B 19K polypeptide (Zhu et al., 1995, which is incorporated herein by reference). The present inventors set out to re-examine the anti-apoptotic activity of these two polypeptides.

HeLa cells were transiently co-transfected with an expression plasmid vector carrying the β-galactosidase gene and a vector carrying a polynucleotide sequence encoding IE1 or IE2. As a positive control, HeLa cells were transiently co-transfected with an expression plasmid vector carrying the β-galactosidase gene and a vector carrying a polynucleotide sequence encoding an anti-apoptotic polypeptide, such as the adenovirus E1B 19K or baculovirus p35. As a negative control, HeLa cells were transiently co-transfected with an expression plasmid vector carrying the β-galactosidase gene and a corresponding "empty" expression plasmid vector that does not carry a polynucleotide sequence encoding IE1, IE2, or a polypeptide having anti-apoptotic activity.

Figure 5:
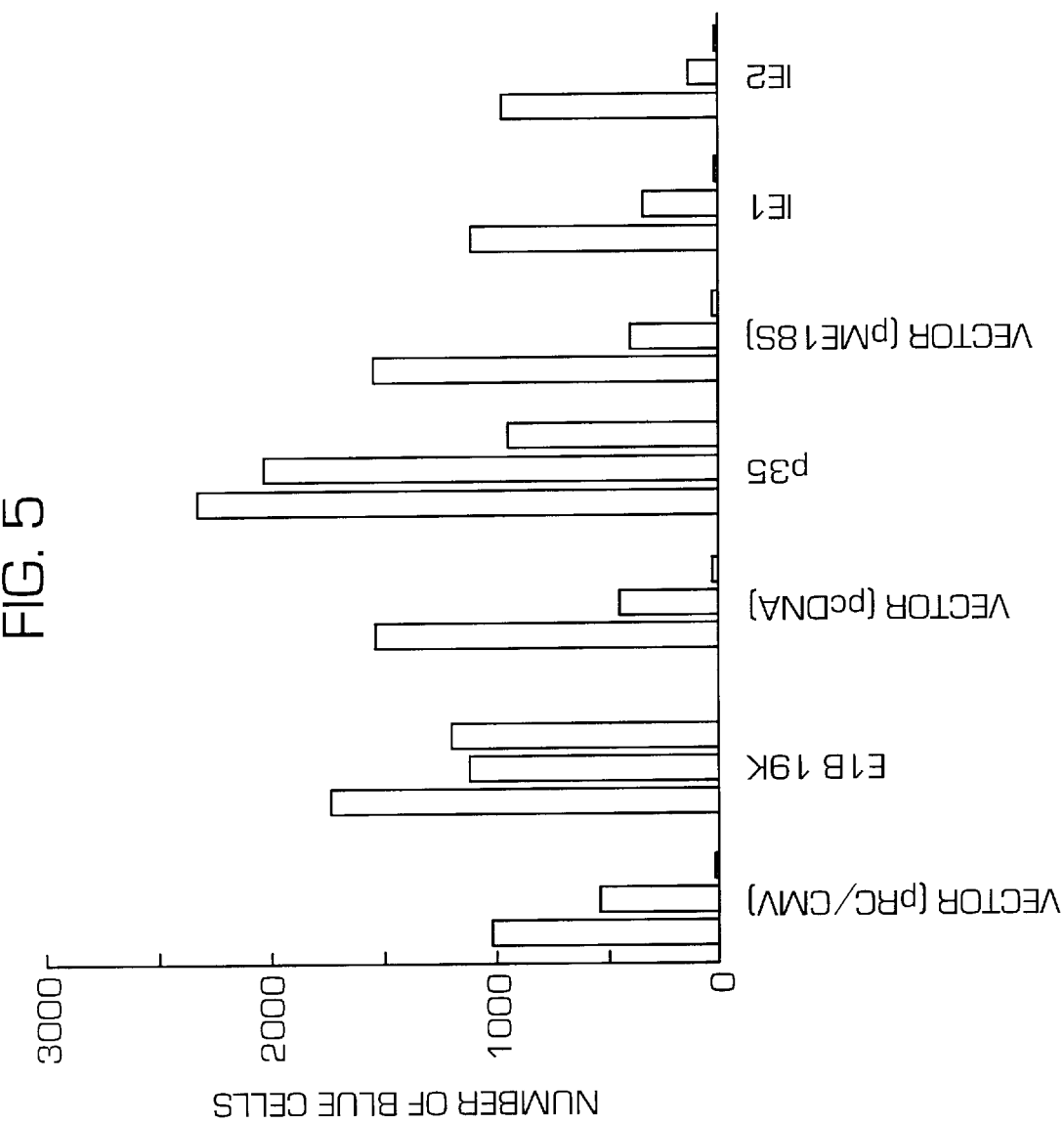
FIG. 5 is a histogram that shows the effect of anti-Fas in the presence of cycloheximide (CHX) on HeLa cells expressing the CMV polypeptide IE1 or IE2.

Expression of IE1 (approx. 72 kDa) and IE2 (approx. 86 kDa) in the transfected HeLa cells was confirmed by the Western blot analysis, by immunofluorescence visually examined under a fluorescence microscope, and by transactivation activity which led to an elevation of the vector-CMV-promoter-driven β-galactosidase expression which was increased 2- to 5-fold, as measured by a β-galactosidase ELISA (data not shown). Apoptosis was induced by incubating the transfected cells for 24 h with either TNF-α+CHX, or anti-Fas+CHX. The surviving cells were stained with X-gal, a chromogenic substrate of β-galactosidase, and then the blue-stained cells were scored (FIG. 5).

Nearly all cells transfected with the empty vector were killed. Neither the presence of IE1 nor IE2 offered any protection. In contrast, significant fractions of cells transfected with either E1B 19K or p35 survived. Thus, results of the experiments performed by the present inventors do not support the results of Zhu et al. (1995) that IE1 and IE2 polypeptides can protect HeLa cells against TNF-α-induced apoptosis. Similarly, the present inventors found that IE1 and IE2 polypeptides cannot protect HeLa cells against anti-Fas-induced apoptosis. However, HCMV-infection does protect cells from both apoptotic stimuli. Taken together, these data suggest that HCMV polypeptides, other that IE1 and IE2, are responsible for the protection of cells against apoptosis.

Example 6

Screening of an HCMV DNA Library for HCMV Polynucleotides Encoding Polypeptides having Anti-apoptotic Activity.

To identify HCMV anti-apoptotic gene(s), a genomic HCMV DNA library, carried in Hela cells, was screened. The present inventors found that the ability of the HeLa cells to undergo Fasor TNF-R1-mediated apoptosis was similar to that of MRC-5 fibroblasts. The HeLa cells underwent apoptosis when exposed to either an anti-Fas antibody+CHX or TNF-α+CHX. Both anti-Fas antibodies, 7C11 and Dx2 were tested and capable of inducing apoptosis in HeLa cells, in the presence of CHX (data not shown). However, the induction by Dx2 was marginal.

To construct the HCMV library, HCMV genomic DNA was partially digested with Sau3AI and ligated into the pZeoSV2(+) plasmid expression vector. The average insert size of the library was 3.5 kb (the range 1.7–13 kb). The sequences of the predicted HCMV genes either contain no introns or contain exons that are located in close proximity to each other (Chee et al., 1990, which is incorporated herein by reference) Consequently, the present inventors presumed that the DNA containing the full-length gene sequence could likely be inserted into and carried by a single plasmid.

The screening of the library was based on the present inventors' finding that even a very low concentration (e.g., as low as 0.1% to 1%) of a transfected expression plasmid carrying an anti-apoptotic gene, such as E1B 19K, p 35 (FIG. 6), BCL-$X_L$, or BCL2 (not shown), mixed with a high concentration of an empty vector, could offer a detectable protection of HeLa cells against anti-Fas-induced apoptosis. Thus, 212 pools of the library plasmids (average complexity of 500 colonies/pool) were prepared and the anti-apoptotic activity of these pools of plasmids were compared in HeLa cells. The results for the 26 pools with the highest β-galactosidase activity and a control (the very last bar on the right) are shown in FIG. 7. The pools that gave the strongest β-galactosidase signals, number 176, 205, 145, 209, and 135, were divided into lower complexity sub-pools and evaluated in a similar test.

Finally, individual plasmids from the sub-pools with the highest β-galactosidase activity were re-tested, and those possessing anti-apoptotic activity were isolated. These plasmids exhibited strong anti-apoptotic activity comparable to those plasmids carrying the BCL-$X_L$ and E1B 19K genes, introduced into cells by a similar transient transfection protocol. 5 to 15% of the cell populations transiently transfected with the plasmids carrying the BCL-$X_L$ and E1B 19K genes survived anti-Fas-induced apoptosis, while nearly all cells (greater than 99.9%) in control cultures transfected with the empty vector died, as observed under a microscope.

The DNA inserts were identified by DNA sequencing. These inserts represented two regions of the HCMV genome. The first region contained exon 1 of the UL37 gene with a hypothetical ORF between nucleotides 52,706–52, 215 of the complementary strand of the AD169 genome (Tenney and Colberg-Poley, 1991a,b) coding for a potential polypeptide which was designated as $pUL37_S$. S stands for "short" since UL37 codes for another polypeptide product, $pUL37_L$ ("long") translated from a spliced mRNA covering UL37 exons 1, 2, and 3. The second region contained a hypothetical ORF encoded on the complementary strand in exons 1 and 2 of UL36 representing nucleotides 49,776–48, 246 of the AD169 genome (Tenney and Colberg-Poley, 1991a,b). This ORF encodes a potential polypeptide which was designated as pUL36. Further, this region may encode unspliced or alternatively spliced variants of pUL36 and other polypeptides.

The polypeptide $pUL37_L$ has been previously reported to be expressed by human cells infected with HCMV, and it has been proposed that most of its exon 1 sequence has no functional significance for transactivating activity or intracellular localization (Zhang et al., 1996, which is incorporated herein by reference). However, neither the expression of the hypothetical polypeptide $pUL37_S$ in any cells nor its possible function has been reported.

Example 7

Detection of Anti-apoptotic Activity of HCMV Polypeptides Encoded by Plasmid DNA Transiently Expressed in HeLa Cells.

To confirm that $pUL37_S$ and pUL36 are indeed anti-apoptotic, the regions of DNA closely covering these ORFs were individually generated by PCR, cloned into the mammalian expression vector pCR3.1-uni, and confirmed by DNA sequencing. The present inventors demonstrated that both ORF UL37$_S$, and ORF UL36 protected HeLa cells against anti-Fas-induced apoptosis (FIG. 8).

Since pUL37$_S$ (coded by the unspliced UL37 mRNA with the ORF covering UL37 exon 1) is anti-apoptotic, the present inventors also tested whether pUL37$_L$, a polypeptide coded by the spliced mRNA containing UL37 exon 1, 2, and 3, would similarly be anti-apoptotic. The ORF UL37$_L$ DNA was generated by PCR from a cDNA library made from HCMV-infected cells (see Methods), ligated into an expression vector, sequenced, and the clone tested for its anti-apoptotic activity in HeLa cells. The cDNA rather than genomic DNA was used to express pUL37$_L$ in order to prevent the expression of pUL37$_S$. The results of the test demonstrated that pUL37$_L$ is also anti-apoptotic (FIG. 9).

Example 8
Detection of the Anti-apoptotic Activity of HCMV Polypeptides Encoded by Clones Stably Transformed in HeLa Cells.

HeLa clones continuously (as opposed to transiently) expressing the C-terminal myc-tagged version of pUL37$_S$ were generated by stable transfection. Following the transfection, G418-resistant or puromycin-resistant clones were selected in medium containing G418 (0.7 mg/mL) or puromycin (1 mg/mL), respectively, and then these clones were screened for the expression of the pUL37$_S$-myc-tagged polypeptide by Western analysis with 9E10 anti-Myc antibody. Clones expressing pUL37$_S$-myc (designated HeLa/UL37$_S$) were studied further. Also, G418-resistant clones of HeLa cells and puromycin-resistant clones of HeLa cells, stably transfected with either the empty vector (pcDNA3/myc) or a 10:1 mol/mol mixture of pCDNA3/myc and pPur, were isolated (HeLa/G418 and HeLa/puro, respectively) and used as a negative control in the Western blot analysis and the experiments described below.

The sensitivity of the HeLa/pUL37$_S$ towards Fas- and TNFR-1-mediated apoptosis was tested. The clones were tested and all displayed similar behavior. Virtually none of the HeLa/pUL37$_S$ cells underwent apoptosis induced by anti-Fas or TNF-α, while virtually all control cells (transfected with the empty vector) died.

Example 9
This Example Demonstrates Binding of pUL37$_S$ to Polypeptides Involved in Apoptotic Signaling Pathways, such as FLICE, Bax, BNIP3, Caspase 3 (cpp32), Apaf-1, ICE, Bcl-x$_L$, and Bak. Further, this Example Shows how to Test for Interactions of pUL36, pUL37$_S$, and pUL37$_L$ with any other Polypeptides, Known or Yet Undiscovered, that are Involved in Apoptotic Signaling Pathways.

Figure 10:
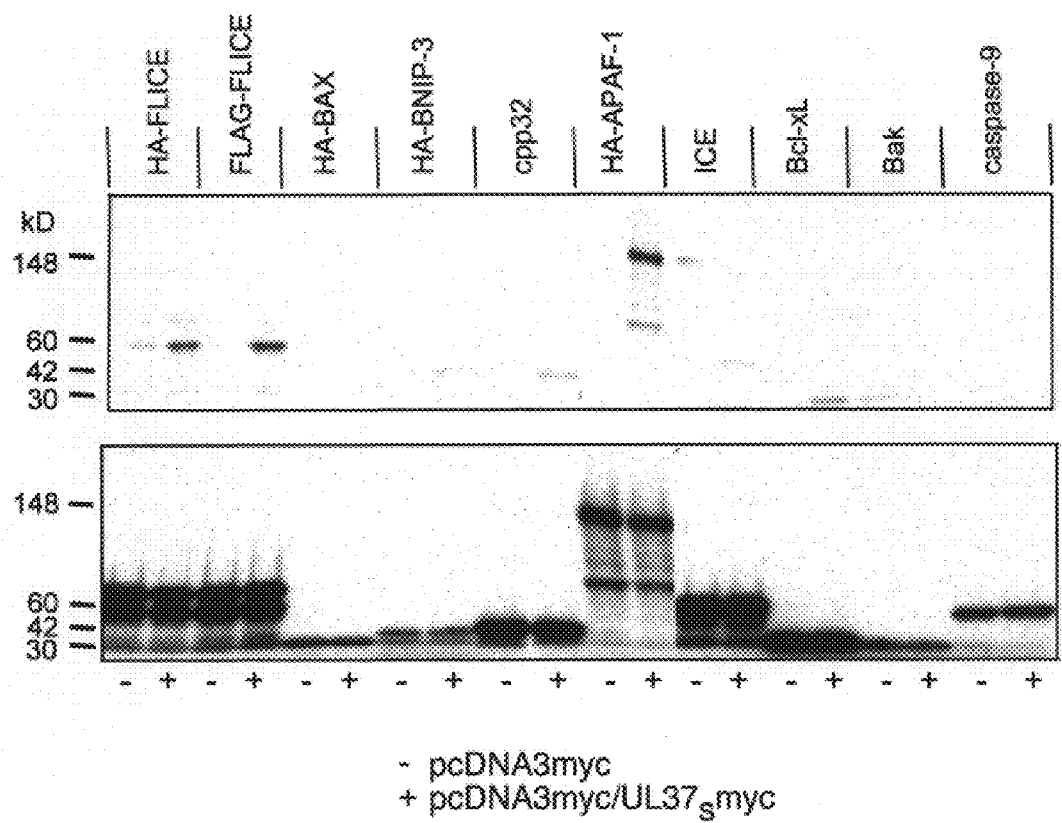
FIG. 10 is an image of polypeptides resolved on a gel demonstrating that, compared to the control agarose beads, the agarose beads with immobilized $pUL37_S$ specifically bind FADD, FLICE, Bax, BNIP3, cpp32 (Caspase 3), Apaf-1, ICE, Bcl-$x_L$, and Bak.

The polypeptide pUL37$_S$ was expressed by transiently transfecting 293 cells with pCDNA3 myc/UL37$_S$ plasmid. Control cells were transfected with pCDNA3 myc plasmid. Two days after transfection, the cells were harvested, lysed in the presence of inhibitors of proteases, and anti-myc antibody was added. The antibody associated with pUL37$_S$myc (or the antibody alone in the control cell lysate) was then bound to protein G immobilized on agarose beads, and the beads containing bound antibody were aliquoted. These aliquots were then incubated with either in-vitro translated FLICE, FLAG-FLICE (FLICE fused to N-terminal FLAG), Bax, BNIP3, Caspase 3 (cpp32), Apaf-1, ICE, Bcl-x$_L$, or Bak, respectively. The incubated bead-protein complex was then washed extensively, and examined for binding of the in-vitro translated polypeptides labeled with $^{35}$S-methionine. The control beads and the bead-protein complex were each boiled in SDS-PAGE sample buffer and analyzed by SDS-PAGE. The results are shown in FIG. 10. The top of FIG. 10 shows that, compared to the control beads, immobilized pUL37$_S$ specifically bound to FLICE, FLAG-FLICE (FLICE fused to N-terminal FLAG), BAX, BNIP3, Caspase 3 (cpp32), Apaf-1, ICE, Bcl-x$_L$, and Bak, but did not bind to Caspase 9. As a control, the bottom of FIG. 10 shows the migration of the respective in-vitro translated polypeptides on the gel.

MATERIALS AND METHODS
Cells and Viruses

Human lung MRC-5 fibroblasts (ATCC CCL 171) and HeLa cells (ATCC CCL 2) were purchased from American Type Culture Collection (ATCC), Rockville, Md. MRC-5 cells were used until passage 25. 293 T cells (DuBridge et al., Mol. Cell. Biol. 7, 379–387 (1987), which is incorporated herein by reference) were purchased from Edge BioSystems, Gaithersburg, Md. Cells were cultured in DMEM supplemented with 10% fetal bovine serum. HCMV AD169 (ATCC VR-538) and Towne (ATCC VR-977) strains were purchased from ATCC. The viral stocks were isolated as follows. Using mother pool virus stock $10^8$ human human MRC-5 fibroblasts were infected with 0.001 plaque forming units (pfu) in 10 ml non-serum-supplemented DMEM in a roller bottle and incubated for 1 hr at 37° C. Medium was then replaced with 100 mL serum-supplemented fresh medium. Medium was changed every 4 days until 100% cells displayed cytopathic effect (CPE). The virus was harvested 5 days after reaching 100% CPE by shaking cells off the bottle and by scraping the remaining cells off into medium. The suspension was centrifuged for 60 min at 10,000 g, the pellet was resuspended in 2 mL serum-free DMEM supplemented with 2 mL sterile skim milk, sonicated on wet ice, spun at 1,000 g for 5 min, and the supernatant containing virus was aliquoted and stored at −80° C.

Antibodies

Mouse monoclonal antibody MA810 reacting with both IE1 and IE2 polypeptides of HCMV and IE2 was purchased from Chemicon International, Temecula, Calif. Mouse monoclonal antibody 7C11 specific for human Fas (CD95) (Robertson et al., 1995, which is incorporated herein by reference) was purchased from Coulter Corp., Miami, Fla. Mouse monoclonal antibody 9E10 reactive with a human c-myc fragment, amino acids 410–419, was purchased from Oncogene Research Products.

Reagents

Cycloheximide (CHX) (Sigma, St. Louis, Mo.) was dissolved in PBS at 10 mg/mL, sterilized by filtering through a 0.22 mm filter and kept as a stock solution at 4° C. Phosphonoacetic acid (Sigma) was dissolved in PBS at 10 mg/mL and sterilized by filtering through a 0.22 mm filter before use. Recombinant human tumor necrosis factor-α (TNF-α) (Sigma, Cat. #T 6674) was reconstituted in sterile water at 10 mg/mL and kept at 4° C. Ganciclovir (Roche Laboratories, Nutley, N.J.) was dissolved in sterile water and kept at −20° C. Z-VADfmc was dissolved in dimethylsulfoxide to the concentration of 50 mM and kept at −20° C. This stock solution was added to cell culture to the final concentration of 80 mM.

Plasmids, Cloning, and Transfection

Green Fluorescent Protein expressing vector pQBI 25 was purchased from Quantum Biotechnologies, Montreal, Canada. pCMVb was purchased from Clontech, San Francisco, Calif. Cosmids containing parts of HCMV AD169 genome, pCM1007, pCM1015, pCM1017, pCM1029, pCM1035, pCM1039, pCM1040, pCM1052, pCM1058, pCM1072 and covering the entire HCMV AD169 genome (Fleckenstein et al., 1982, which is incorporated herein by reference) were used for library constructions. Cosmid pON2601 (Cha et al., 1996, which is incorporated herein by reference) contains a part of the HCMV genome not represented in the AD169 strain. The mammalian expression vectors pZeoSV2(+), pCDNA1.0, pCDNA3, pRC/CMV, pCDNA3.1(−)MycHis, and pCR3.1-Uni were purchased from Invitrogen, Carlsbad, Calif. pCDNA3/Myc$_3$ is a derivative of pCDNA3 into which has been cloned a DNA sequence encoding three copies of the human c-myc peptide corresponding to amino acids 408–421 within the carboxy terminal domain of human cMyc of human origin.

The cDNA encoding pro- and anti-apoptotic polypeptides were subcloned into the mammalian expression vectors pCDNA3, pCDNA1.0, and/or pRC/CMV (Invitrogen) and/or their derivatives containing either N-terminal FLAG, N-terminal HA, or C-terminal myc peptide as described in the text. The mammalian expression plasmids carrying IE1, pON 2205 and IE2, pON2206 were described previously (Jenkins et al., 1994, which is incorporated herein by reference). The UL37$_S$, UL37$_L$, and UL36 sequences were generated by PCR and cloned in various mammalian expression vectors as described in the text. The fidelity of PCR products and of cloning was always confirmed by DNA sequencing. Unless specified otherwise, transfections were performed with SuperFect (Qiagen, Valencia, Calif.) in accordance with the manufacturer's recommendations. Some transfections were done with LipofectAMINE (GIBCO-BRL, Gaithersburg, Md.) with similar results.

Construction of CMV DNA Libraries

A genomic DNA library was cloned into pZeoSV2(+) plasmid (Invitrogen). Ten cosmids covering the AD169 genome were mixed in equal amounts and partially digested with Sau3AI (New England Biolabs, Beverly, Mass.), then fragments of 2–5 kb were size-selected on an agarose gel and ligated into the BamHI site of pZeoSV2(+). Library complexity ~3×10$^5$ colonies; the average insert size 3.5 kb (the range 1.7–13 kb). A cDNA library was constructed as follows. MRC-5 fibroblasts were infected with HCMV AD 169 at approximately 5–15 pfu/cell, then 27 h later mRNA was isolated with FastTrack 2.0 kit (Invitrogen) in accordance with the manufacturer's protocol, and then the first strand cDNA was synthesized with a SuperScript Preamplification System for First Strand cDNA Synthesis (GIBCO-BRL) in accordance with the manufacturer's protocol. This cDNA preparation was used for PCR.

Various Molecular Biology Methods

PCR, Western blot analysis, DNA sequencing, DNA cloning, and X-gal staining of cells for β-galactosidase detection was done by standard procedures described in Sambrook et al. (1989), which is incorporated herein by reference.

REFERENCE LIST

Al-Barazi, H. O., and Colberg-Poley, A. M. (1996) The human cytomegalovirus UL37 immediate-early regulatory protein is an integral membrane N-glycoprotein which traffics through the endoplasmic reticulum and Golgi apparatus. J. Virol. 70, 7198–7208.

Bertin, J., Armstrong, R. C., Ottilie, S., Martin, D. A., Wang Y., Banks S., Wang G.-H., Senkevich, T. G., Alnemri, E. S., Moss, B., Lenardo, M. J., Tomaselli, K. J., and Cohen, J. I. (1997) Death effector domain-containing herpesvirus and poxvirus proteins inhibit both Fas- and TNFR1-induced apoptosis. Proc. Natl. Acad. Sci. USA 94, 1172–1176.

Boldogh, I., AbuBakar, S., Deng, C. Z., and Albrecht, T. (1991) Transcriptional activation of cellular oncogenes fos, jun, and myc by human cytomegalovirus. J. Virol. 65, 1568–1571.

W. J. Britt, C. A. Alford: Cytomegalovirus. In *Fields Virology, Third Edition* (B. N. Fields, D. M. Knipe, P. M. Howley et al., ed) Lippincott-Raven Publishers, Philadelphia, pp. 2493–2523, 1996.

Brooks, M. A., Ali, A. N., Turner, P. C., and Moyer, R. W. A rabbitpox virus serpin gene controls host range by inhibiting apoptosis in restrictive cells. (1995) J. Virol. 69, 7688–7698.

Cha, T.-A., Tom, E., Kemble, G. W., Duke, G. M., Mocarski, E. S., and Spaete, R. R. (1996) Human cytomegalovirus clinical isolates carry at least 19 genes not found in laboratory strains. J. Virol. 70, 78–83.

Chee, M. S., Bankier, A. T., Beck, S., Bohni, R., Brown, C. M., Cerny, R., Horsnell, T., Hutchison, C. A., Kouzarides, T., Martignetti, J. A., Preddie, E., Satchwell, S. C., Tomlinson, P., Weston, K. M., and Barrell, B. G. (1990) Analysis of the protein-coding content of the sequence of human cytomegalovirus strain AD169. Curr. Top. Microb. Immunol. 154, 125–169.

Clem, R. J., Fechheimer, M., and Miller, L. K. (1991) Prevention of apoptosis by a baculovirus gene during infection of insect cells. Science 254, 1388–1390.

Crumpacker, C. S. (1996) Gancyclovir. New Engl. J. Med. 335, 721–729.

R. C. Duke, D. M. Ojcius, J. D.-E. Young: Cell Suicide in Health and Disease. *Scientific American*, December 1996: 80–87.

Evan, G. I., Wyllie, A. H., Gilbert, C. S., Littlewood, T. D., Land, H., Brooks, M., Waters, C. M., Penn, L. Z., and Hancock, D. C. (1992) Induction of apoptosis in fibroblasts by c-myc protein. Cell, 69, 119–128.

Fleckenstein, B., Muller, I., and Collins, J. (1982) Cloning of the complete human cytomegalovirus genome in cosmids. Gene 18, 39–46.

Fries, K. L., Miller, W. E., and Raab-Traub, N. (1996) Epstein-Barr virus latent membrane protein 1 blocks p53-mediated apoptosis through the induction of the A20 gene. J. Virol. 70, 8653–8659.

Geist, L. J., Monick, M. M., Stinski, M. F., and Hunninghake, G. W. (1994) The immediate early genes of human cytomegalovirus upregulate tumor necrosis factor-a gene expression. J. Clin. invest. 93, 474–478.

Gooding, L. R., Elmore, L. W., Tollefson, A. E., Brady, H. A., and Wold, W. S. M. A 14,700 MW protein from the E3 region of adenovirus inhibits cytolysis by tumor necrosis factor. Cell 53, 341–346.

Heller, R. A., and Kronke, M. (1994) Tumor necrosis factor receptor-mediated signalling pathways. J. Cell Biol. 126, 5–9.

Henderson, S., Rowe, M., Gregory, C., Croom-Carter, D., Wang, F., Longnecker, R., Kieff, E., and Rinkinson, A. (1991) Induction of bcl-2 expression by Epstein-Barr virus latent membrane protein 1 protects infected B-cells from programmed cell death. Cell 65, 1107–1115.

Henderson, S., Huen, D., Rowe, M., Dawson, C., Johnson, G., and Rickinson, A. Epstein-Barr virus-coded BHRF1 protein, a viral homologue of Bcl-2, protects human B cells from programmed cell death. Proc. Natl. Acad. Sci. USA 90, 8479–8483.

Hershberger, P. A., Dickson, J. A., and Friesen, P. D. (1992) Site-specific mutagenesis of the 35-kilodalton protein gene encoded by *Autographa californica* nuclear polyhedrosis virus: cell line-specific effects on virus replication. J. Virol. 66, 5525–5533.

M. S. Hirsch: Cytomegalovirus Infection. In *Harrison's Principle of Internal Medicine, Thirteenth Edition* (K.J. Isselbacher et al., ed) McGraw-Hill, Inc. Health Professions Division, New York, pp 794–796, 1994.

Hu, S., Vincenz, C., Buller, M., and Dixit, V. M. (1997) A novel family of viral death effector domain-containing molecules that inhibit both CD-95- and tumor necrosis factor receptor-1-induced apoptosis. J. Biol. Chem. 272, 9621–9624.

Huang, E.-S. (1975) Human cytomegalovirus. IV. Specific inhibition of virus-induced DNA polymerase activity and viral DNA replication by phosphonoacetic acid. J. Virol. 16, 1560–1565.

Huang, E.-S., and Kowalik, T. F. (1993). The pathogenicity of human cytomegalovirus: an overview. In: Molecular aspects of human cytomegalovirus diseases (Becker, Y., Darai, G., and Huang, E.-S., Eds.) Springer-Verlag, Berlin, pp. 3–45.

Jenkins, D. E., Martens, C. L., and Mocarski, E. S. (1994) Human cytomegalovirus late protein encoded by ie2: a trans-activator as well as a repressor of gene expression. J. Gen. Virol. 75, 2337–2348.

Kagi, D., Vignaux, F., Ledermann, B., Burki, K., Depraetere, V., Nagata, S., Hengartner, H., and Goldstein, P. Science 265, 528–530.

Kettle, S., Alcami, A., Khanna, A., Ehret, R., Jassoy, C., and Smith, G. L. (1997) Vaccinia virus serpin B1 3R (SPI-2) inhibits interleukin-1b-converting enzyme and protects virus-infected cells from TNF- and Fas-mediated apoptosis, but does not prevent IL-1b-induced fever. J. Gen. Virol. 78, 677–685.

Ko, L. J., and Prives, C. (1996) p53: puzzle and paradigm. Gen. & Dev. 10, 1054–1072.

Kovacs, A., Weber, M. L., Burns, L. J., Jacob, H. S., and Vercellotti, G. M. Cytoplasmic sequestration of p53 in cytomegalovirus-infected human endothelial cells. Am. J. Pathol. 149, 1531–1539.

J. P. Lalezari et al.: Intravenous Cidofovir for Peripheral Cytomegalovirus Retinitis in Patients with AIDS. A Randomized, Controlled trial. *Annals of Internal Medicine* 126: 257–263, 1997.

Leopardi, R., and Roizman, B. (1996) The herpes simplex virus major regulatory protein ICP4 blocks apoptosis induced by the virus or by hyperthermia. Proc. Natl. Acad. Sci. USA 93, 9583–9587.

Leopardi, R., Sant, C. V., and Roizman, B. (1997) The herpes simplex virus 1 protein kinase $U_S3$ is required for protection from apoptosis induced by the virus. Proc. Natl. Acad. Sci. USA 94, 7891–7896.

Li, P., Nijhawan, D. Budihardjo, I., Srinivasula, S. M., Ahmad, M., Alnemri, E. S., and Wang, X. (1997) Cytochrome c and dATP-dependent formation of Apaf-1/caspase-9 complex initiates an apoptotic protease cascade. Cell 91, 479–489.

Mestan, J., Digel, W., Mittnacht, S., Hillen, H., Blohm, d., Moller, A., Jacobsen, H., and Kirchner, H. (1986) Nature 323, 816–819.

E. S. Mocarski, Cytomegaloviruses and Their Replication. In *Fields Virology, Third Edition* (B. N. Fields, D. M. Knipe, P. M. Howley et al., ed) Lippincott-Raven Publishers, Philadelphia, pp 2447–2492, 1996.

Morgenstern, J. P., and Land, H. (1991) Choice and manipulation of retroviral vectors. In: Methods in Molecular Biology, Vol. 7, pp. 181–205, The Humana Press, Clifton, N.J.

Muganda, P., Mendoza, O., Hernandez, J., and Qian, Q. (1994) Human cytomegalovirus elevates levels of the cellular protein p53 in infected fibroblasts. J. Virol. 68, 8028–8034.

Nava, V. E., Cheng, E. H.-Y., Veliuona, M., Zou, S., Clem, R. J., Mayer, M. L., and Hardwick, J. M. (1997) Herpesvirus Saimiri encodes a functional homolog of the human bcl-2 oncogene. J. Virol. 71, 4118–4122.

Pilder, S., Logan, J., and Shenk, T. (1984) Deletion of the gene encoding the adenovirus 5 early region 1b 21,000-molecular-weight polypeptide leads to degradation of viral and host cell DNA. J. Virol. 52, 664–671.

Razvi, E. S., an d Welsh, R. M. (1995) Apoptosis in viral infections. Adv. Virus Res. 45, 1–60.

B. Roizman: Herpesviridae: A Brief Introduction. In *Fundamental Virology, Second Edition* (B. N. Fields, D. M Knipe et al., ed) Raven Press, New York, pp 841–847, 1991.

Robertson, M. J., Manley, T. J., Pichert, G., Cameron, C., Cochran, K. J., Levine, H., and Ritz, J. (1995) Functional consequences of APO-1/Fas (CD95) antigen expression by normal and neoplastic hematopoietic cells. Leuk. Lymph. 17, 51–61.

Salvesen, G. S., and Dixit, V. M. (1997) Caspases: intracellular signaling by proteolysis. Cell 91, 443–446.

Sambrook, J., Fritsch, E. F., and Maniatis, T. (1989) Molecular cloning. 2nd edition. Cold Spring Harbor Laboratory Press.

Sarid, R., Sato, T., Bohenzky, R. A., Russo, J. J., and Chang, Y. (1997) Kaposi's sarcoma-associated herpesvirus encodes a functional Bcl-2 homologue. Nature Med. 3, 293–298.

Sedger, L., and McFadden, G. (1996) M-T2: a poxvirus TNF receptor homologue with dual activities. Immunol. Cell Biol. 74, 538–545.

Y. Shen, T. E. Shenk: Viruses and Apoptosis. *Curr. Opin. Gen. Dev.* 5: 105–111, 1995.

Sieg, S., Yildirim, Z., Smith, D., Kayagaki, N., Yagita, H., Huang, Y., and Kaplan, D. (1996) Herpes simplex virus type 2 inhibition of Fas ligand expression. J. Virol. 70, 8747–8751.

Smith, P. D., Saini, S. S., Raffeld, M., Manischewitz, J. F., and Wahl, S. M. (1992) Cytomegalovirus induction of tumor necrosis factor-a by human monocytes and mucosal macrophages. J. Clin. Invest. 90, 1642–1648.

Soneoka, Y., Cannon, P. M., Ramsdale, E. E., Griffiths, J. C., Romano, G., Kingsman, S. M., and Kingsman, A. J. (1995) A transient three-plasmid expression system for the production of high titer retroviral vectors. Nucl. Acids Res. 23, 628–633.

Speir, E., Modali, R., Huang, E.-S., Leon, M. B., Shawl, F., Finkel, T., and Epstein, S. E. (1994) Potential role of human cytomegalovirus and p53 interaction in coronary restenosis. Science 265, 391–394.

Subramanian, T., Kuppuswamy, M., Gysbers, J., Mak, S., and Chinnadurai, G. (1984) !9 kDa tumor antigen coded by early region E1b of adenovirus 2 is required for efficient synthesis and for protection of viral DNA. J. Biol. Chem. 259, 11777–11783.

Tenney, D. J., and Colberg-Poley, A. M. (1991a) Expression of the human cytomegalovirus UL36–38 immediate early region during permissive infection. Virology 182, 199–210.

Tenney, D. J., and Colberg-Poley, A. M. (1991b) Human cytomegalovirus UL36–38 and US3 immediate-early genes: temporally regulated expression of nuclear, cytoplasmic, and polysome-associated transcripts during infection. J. Virol. 65, 6724–6734.

Teodoro, J. G., and Branton, P. E. (1997) Regulation of apoptosis by viral gene products. J. Virol. 71, 1739–1746.

C. B. Thompson: Apoptosis in the Pathogenesis and Treatment of Disease. *Science* 267: 1456–1462, 1995.

D. L. Vaux, G. Haecker, A. Strasser: An Evolutionary Perspective on Apoptosis. *Cell* 76: 777–779. 1994.

D. L. Vaux, A. Strasser: The Molecular Biology of Apoptosis. *Proc. Natl. Acad. Sci. USA* 93: 2239–2244, 1996.

Vilcek, J., and Sen, G. C. (1996) Interferons and other cytokines in Fields Virology, 3rd ed., B. N. Fields, D. M. Knipe, P. M. Howley et al., eds Lippincott-Raven, Philadelphia, Pa., 375–399.

Wang, S., Rowe, M., and Lundgren, E. (1996) Expression of the Epstein-Barr virus transforming protein LMP1 causes a rapid and transient stimulation of the Bcl-2 homologue Mcl-1 levels in b-cell lines. Cancer Res. 56, 4610–4613.

D. O. White, F. J. Fenner: *Medical Virology, Fourth Edition*, Academic Press, San Diego, Chapters 16 and 20, 1994.

Wong, G. H. W., and Goeddel, D. V. (1986) Nature, 323, 819–822.

Zhang, H., Al-Barazi, H. O., and Colberg-Poley, A. M. Virology 223, 292–302 (1996).

Zhu, H., Shen, Y., and Shenk, T. (1995) Human cytomegalovirus IE1 and IE2 proteins block apoptosis. J. Virol. 69, 7960–7970.

What is claimed is:

1. An isolated or synthetic polypeptide that comprises a human cytomegalovirus (HCMV) polypeptide, wherein said HCMV polypeptide is $pUL37_S$, and wherein said isolated or synthetic polypeptide has anti-apoptotic activity in a cell and is not $pUL37_L$.

* * * * *